(12) United States Patent
Allison et al.

(10) Patent No.: US 10,023,637 B2
(45) Date of Patent: Jul. 17, 2018

(54) COMBINATION IMMUNOTHERAPY FOR THE TREATMENT OF CANCER

(71) Applicants: Board of Regents, The University of Texas System, Austin, TX (US); Memorial Sloan-Kettering Cancer Center, New York, NY (US)

(72) Inventors: James Allison, New York, NY (US); Padmanee Sharma, Bellaire, TX (US); Sergio A. Quezada, Berkhamsted (GB); Tihui Fu, Houston, TX (US)

(73) Assignees: Board of Regents, The University of Texas System, Austin, TX (US); Memorial Sloan-Kettering Cancer Center, New York, NY (US)

( * ) Notice: Subject to any disclaimer, the term of this patent is extended or adjusted under 35 U.S.C. 154(b) by 205 days.

(21) Appl. No.: 15/145,780

(22) Filed: May 3, 2016

(65) Prior Publication Data
US 2016/0244524 A1 Aug. 25, 2016

Related U.S. Application Data

(62) Division of application No. 14/250,272, filed on Apr. 10, 2014, now Pat. No. 9,375,475, which is a division of application No. 13/498,570, filed as application No. PCT/US2010/051008 on Sep. 30, 2010, now Pat. No. 8,709,417.

(60) Provisional application No. 61/247,438, filed on Sep. 30, 2009.

(51) Int. Cl.
| | | |
|---|---|---|
| *C07K 16/28* | (2006.01) | |
| *A61K 39/395* | (2006.01) | |
| *A61K 38/17* | (2006.01) | |
| *A61K 39/00* | (2006.01) | |

(52) U.S. Cl.
CPC ...... *C07K 16/2818* (2013.01); *A61K 38/1709* (2013.01); *A61K 39/3955* (2013.01); *A61K 39/39558* (2013.01); *C07K 16/2803* (2013.01); *A61K 2039/505* (2013.01); *A61K 2039/507* (2013.01); *C07K 2317/73* (2013.01); *C07K 2317/74* (2013.01)

(58) Field of Classification Search
None
See application file for complete search history.

(56) References Cited

U.S. PATENT DOCUMENTS

| | | | |
|---|---|---|---|
| 6,051,227 | A | 4/2000 | Allison et al. |
| 6,521,749 | B1 | 2/2003 | Ling et al. |
| 6,808,710 | B1 | 10/2004 | Wood et al. |
| 6,984,720 | B1 | 1/2006 | Korman et al. |
| 7,521,051 | B2 | 4/2009 | Collins et al. |
| 7,595,048 | B2 | 9/2009 | Honjo et al. |
| 7,722,868 | B2 | 5/2010 | Freeman et al. |
| 7,722,872 | B2 | 5/2010 | Kroczek |
| 7,943,743 | B2 | 5/2011 | Korman et al. |
| 8,008,449 | B2 | 8/2011 | Korman et al. |
| 8,017,114 | B2 | 9/2011 | Korman et al. |
| 8,168,179 | B2 | 5/2012 | Honjo et al. |
| 8,354,509 | B2 | 1/2013 | Carven et al. |
| 8,383,796 | B2 | 2/2013 | Korman et al. |
| 8,652,465 | B2 | 2/2014 | Freeman et al. |
| 8,709,417 | B2 | 4/2014 | Allison et al. |
| 8,728,474 | B2 | 5/2014 | Honjo et al. |
| 8,900,587 | B2 | 12/2014 | Carven et al. |
| 8,952,136 | B2 | 2/2015 | Carven et al. |
| 9,084,776 | B2 | 7/2015 | Korman et al. |
| 9,102,725 | B2 | 8/2015 | Korman et al. |
| 9,273,135 | B2 | 3/2016 | Korman et al. |
| 9,358,289 | B2 | 6/2016 | Korman et al. |
| 9,375,475 | B2 | 6/2016 | Allison et al. |
| 9,387,247 | B2 | 7/2016 | Korman et al. |
| 9,492,539 | B2 | 11/2016 | Korman et al. |
| 9,492,540 | B2 | 11/2016 | Korman et al. |
| 9,580,505 | B2 | 2/2017 | Korman et al. |
| 9,580,507 | B2 | 2/2017 | Korman et al. |
| 9,738,718 | B2 * | 8/2017 | Liu .................. C07K 16/2896 |
| 2003/0044768 | A1 * | 3/2003 | Wood ................ G01N 33/505 435/4 |
| 2003/0124149 | A1 | 7/2003 | Shalaby et al. |
| 2003/0232323 | A1 | 12/2003 | Freeman et al. |
| 2004/0213795 | A1 * | 10/2004 | Collins ............ C07K 16/2803 424/155.1 |
| 2005/0085433 | A1 | 4/2005 | Breidenstein |
| 2007/0122378 | A1 | 5/2007 | Freeman et al. |
| 2008/0069795 | A1 | 3/2008 | Rabb |
| 2008/0279851 | A1 * | 11/2008 | Coyle ................ C07K 16/2818 424/133.1 |
| 2009/0217401 | A1 | 8/2009 | Korman et al. |

(Continued)

FOREIGN PATENT DOCUMENTS

| | | |
|---|---|---|
| CN | 1371416 A | 9/2002 |
| CN | 101355965 A | 1/2009 |

(Continued)

OTHER PUBLICATIONS

Sanmamed et al. (2015) Semin Oncol 42: 640-655.*
Ara, G., et al., "Potent Activity of Soluble B7RP-1-Fc in Therapy of Murine Tumors in Syngeneic Hosts," *Int. J Cancer*, 103(4): 501-507 (2002).
Arimura, Y., et al., "A Co-Stimulatory Molecule on Activated T Cells, H4/ICOS, Delivers Specific Signals in $T_h$ Cells and Regulates Their Responses," *Int'l Immuno.*, 14(6): 555-566 (2002).
Bakkour, S. and Sha, W.C., "Mapping of the ICOS Binding Surface of Murine B7h Using an Unbiased, Cellular Library of B7h Mutants Created by Cyclical Packaging Rescue," *J. Immuno. Methods*, 332: 151-161 (2008).

(Continued)

*Primary Examiner* — Ilia I Ouspenski
(74) *Attorney, Agent, or Firm* — Hamilton, Brook, Smith & Reynolds, P.C.

(57) ABSTRACT

Agonists to ICOS in combination with a blocking agent to a T cell inhibitory receptor (e.g., CTLA-4, PD-1, etc.) are demonstrated herein to be useful for the treatment of tumors.

19 Claims, 13 Drawing Sheets

(56) References Cited

U.S. PATENT DOCUMENTS

| | | | |
|---|---|---|---|
| 2012/0251556 | A1 | 10/2012 | Allison et al. |
| 2014/0002102 | A1 | 1/2014 | Rangarajan et al. |
| 2014/0308299 | A1 | 10/2014 | Allison et al. |
| 2014/0314714 | A1 | 10/2014 | Honjo et al. |
| 2015/0093380 | A1 | 4/2015 | Honjo et al. |
| 2015/0232555 | A1 | 8/2015 | Carven et al. |
| 2016/0304606 | A9 | 10/2016 | Carven et al. |
| 2016/0304610 | A1* | 10/2016 | Sazinsky ............ C07K 16/2818 |

FOREIGN PATENT DOCUMENTS

| | | |
|---|---|---|
| JP | 2002-531416 | 9/2002 |
| JP | 2006-265155 | 10/2006 |
| JP | 2007-277242 | 10/2007 |
| JP | 2008-543774 | 12/2008 |
| WO | WO 2000/32231 | 6/2000 |
| WO | WO 2001/14557 A1 | 3/2001 |
| WO | WO 2002/00692 A2 | 1/2002 |
| WO | WO 2002/00730 A2 | 1/2002 |
| WO | WO 2003/042402 A2 | 5/2003 |
| WO | WO 2004/004771 A1 | 1/2004 |
| WO | WO 2006/121168 A1 | 11/2006 |
| WO | WO 2006/133396 | 12/2006 |
| WO | WO 2007/005874 A2 | 1/2007 |
| WO | WO 2007/113648 | 10/2007 |
| WO | 2008/085562 A2 | 7/2008 |
| WO | WO 2008/137915 A2 | 11/2008 |
| WO | WO 2008/156712 A1 | 12/2008 |
| WO | WO 2012/131004 A2 | 10/2012 |
| WO | 2016/120789 A1 | 8/2016 |
| WO | WO 2016/154177 | 9/2016 |

OTHER PUBLICATIONS

Beier, K.C., et al., "Induction, Binding Specificity and Function of Human ICOS," *Eur. J Immunol.*, 30: 3707-3717 (2000).

Bertino, S.A., et al., "Roquin Paralogs Add a New Dimension to ICOS Regulation," *Immunity*, 38(4): 624-626 (2013).

Blazar, B.R., "Infusion of anti-B7.1 (CD80) and anti-B7.2 (CD86) monoclonal antibodies inhibits murine graft-versus-host disease lethality in part via direct effects on CD4+ and CD8+ T cells," *J. Immunol.*, 157(8): 3250-3259 (1996).

Boon, T., et al., "Human T cell responses against melanoma," *Annu. Rev. Immunol.*, 24: 175-208 (2006).

Callahan, M.K., et al., "Anti-CTLA-4 antibody therapy: Immune monitoring during clinical development of a novel immunotherapy," *Semin. Oncol.*, 37(5): 473-484 (2010).

Carthon, B.C., et al., "Preoperative CTLA-4 Blockade: Tolerability and Immune Monitoring in the Setting of a Presurgical Clinical Trial," *Clin. Cancer Res.*, 16: 2861-2871 (2010).

Chattopadhyay, K., et al., "Structural Basis of Inducible Costimulator Ligand Costimulatory Function: Determination of the Cell Surface Oligomeric State and Functional Mapping of the Receptor Binding Site of the Protein," *J. Immuno.*, 177: 3920-3929 (2006).

Chen, H., et al., "Anti-CTLA-4 Therapy Results in Higher CD4+ICOS$^{hi}$ T Cell Frequency and IFN-γ Levels in Both Nonmalignant and Malignant Prostate Tissues," *PNAS*, 106(8): 2729-2734 (2009).

Chen, H., et al., "CD4 T Cells Require ICOS-Mediated PI3K Signaling to Increase T-Bet Expression in the Setting of Anti-CTLA-4 Therapy," *Cancer Immunol. Res.*, 2(2): 167-176 (2013).

Conrad, C., et al., "Plasmacytoid dendritic cells promote immunosuppression in ovarian cancer via ICOS costimulation of Foxp3(+) T-regulatory cells," *Cancer Res.*, 72(20): 5240-5249 (2012).

Deng, Z.B., et al., "An Agonist Human ICOS Monoclonal Antibody that Induces T Cell Activation and Inhibits Proliferation of a Myeloma Cell Line," *Hybridoma and Hybridomics*, 23(3): 176-182 (2004).

Di Giacomo, A.M., et al., "Long-Term Survival and Immunogical Parameters in Metastatic Melanoma Patients Who Responded to Ipilimumab 10 mg/kg Within an Expanded Access Programme," *Cancer Immunol. Immunother.*, 62(6): 1021-1028 (2013).

Dianzani, C., et al., "B7h Triggering Inhibits the Migration of Tumor Cell Lines," *J. Immuno.*, 192(10): 4921-4931 (2014).

Dong et al. "Tumor-associated B7-H1 promotes T-cell apoptosis: A potential mechanism of immune evasion," 8 *Nature Medicine* 793 (Aug. 2002) (published online Jun. 24, 2002).

Driessens, G., et al., "Costimulatory and coinhibitory receptors in anti-tumor immunity," *Immunol. Rev.*, 229(1): 126-144 (2009).

EP 10821297.8 Supplementary European Search Report dated Jul. 9, 2013.

Faget, J. et al., "ICOS-ligand expression on plasmacytoid dendritic cells supports breast cancer progression by promoting the accumulation of immunosuppressive CD4+T cells," *Cancer Res.*, 72: 6130-6141 (2012).

Faget, J., et al., "ICOS Is Associated with Poor Prognosis in Breast Cancer As It Promotes the Amplification of Immunosuppresive CD4+ T Cells by Plasmacytoid Dendrite Cells," *OncoImmunology*, 2(3): 1-3(2013).

Freeman et al., "Engagement of the PD-1 Immunoinhibitory Receptor by a Novel B7 Family Member Leads to Negative Regulation of Lymphocyte Activation," 192 *J. Exp. Med.* 1027 (Oct. 2, 2000).

Fu, T., et al., "The ICOS/ICOSL Pathway is Required for Optimal Antitumor Responses Mediated by Anti-CTLA-4 Therapy," *Cancer Res.*, 71, 5445-5454 (2011).

Greenwald, R.J. et al. "The B7 Family Rev s ted," *Ann. Rev. Immunol.*, 23:515-48 (2005).

Harada, Y., et al., A Single Amino Acid Alteration in Cytoplasmic Domain Determines IL-2 Promoter Activation by Ligation of CD28 but Not Inducible Costimulator (ICOS), *J. Exp. Med.*, 197(2): 257-262 (2003).

Heissmeyer, V. and Vogel, K.U., "Molecular Control of Tfh-Cell Differentiation by Roquin Family Proteins," *Immunological Reviews*, 253: 273-289 (2013).

Hu, H., et al., "Noncanonical NF-κB Regulated Inducible Costimulator (ICOS) Ligand Expression and T Follicular Helper Cell Development," *PNAS*, 108(31):12827-12832 (2011).

Huang, Z., "Structural chemistry and therapeutic intervention of protein-protein interactions in immune response, human immunodeficiency virus entry, and apoptosis," *Pharmacol. Ther.*, 86(3): 201-215 (2000).

Hutloff, A., et al., "ICOS is an Inducible T-Cell Co-Stimulator Structurally and Functionally Related to CD28," *Nature*, 397: 263-266 (1999).

Inman, B.A., et al., "Costimulation, Coinhibition and Cancer," *Curr. Can. Drug. Targets*, 7(1): 15-30 (2007).

Khayyamian, S., et al., "ICOS-ligand, expressed on human endothelial cells, costimulates Th1 and Th2 cytokine secretion by memory CD4+T cells," *PNAS*, 99 (9): 6198-6203 (2002).

Kosuge, H., et al., "Induction of Immunologic Tolerance to Cardiac Allograft by Simultaneous Blockade of Inducible Co-Stimulator and Cytotoxic T-Lymphocyte Antigen 4 Pathway," *Transplantation*, 75(8): 1374-1379 (2003).

Latchman et al., "PD-L2 is a second ligand for PD-1 and inhibits T cell activation," 2 *Nature Immunology* 261 (Mar. 2001).

Lee, K.H., et al., "Increased vaccine-specific T cell frequency after peptide-based vaccination correlates with increased susceptibility to in vitro stimulation but does not lead to tumor regression," *J. Immunol.*, 163(11): 6292-6300 (1999).

Liakou, C., et al., "CTLA-4 blockade increases IFNγ-producing CD4+ICOS$^{hi}$ cells to shift the ratio of effector to regulatory T cells in cancer patients," *PNAS*, 105 (39): 14987-14992 (2008).

Ling, V., et al., "Differential Expression of Inducible Costimulator-Ligand Splice Variants: Lymphoid Regulation of Mouse GL50-B and Human GL50 Molecules," *J. Immunol.*, 166: 7300-7308 (2001).

Lischke, T., et al., "Comprehensive Analysis of CD4+ T Cells in the Decision Between Tolerance and Immunity In Vivo Reveals a Pivotal Rolse for ICOS," *J. Immunol.*, 1-11 (2012).

Liu, X., et al., "B7H costimulates clonal expansion of, and cognate destruction of tumor cells by, CD8+T lymphocytes in vivo," *J. Exp. Med.*, 194(9): 1339-1348 (2001).

(56) References Cited

OTHER PUBLICATIONS

Mages, H.W., et al., "Molecular Cloning and Characterization of Murine ICOS and Identification of B7h as ICOS Ligand," *Eur. J. Immunol.*, 30: 1040-1047 (2000).
Martin-Orozco, N., et al., "Melanoma Cells Express ICOS Ligand to Promote the Activation and Expansion of T-Regulatory Cells," *Cancer Res.*, 70(23): 9581-9590 (2010).
McAdam, A.J., et al., "Mouse Inducible Costimulatory Molecule (ICOS) Expression is Enhanced by CD28 Costimulation and Regulates Differentiation of CD4$^+$T Cells," *J. Immuno.*, 165: 5035-5040 (2000).
Nabeyama, K., et al., "Beneficial Effects of Costimulatory Blockade with Anti-Inducible Costimulator Antibody in Conjunction with CTLA4Ig on Prevention of Islet Xenograft Rejection from Rat to Mouse," *Transplantation*, 78 (11): 1590-1596 (2004).
Nanji, S.A., "Multiple Combination Therapies Involving Blockade of ICOS/B7RP-1 Costimulation Facilitate Long-Term Islet Allograft Survival," *Am J of Transplantation*, 4:526-536 (2004).
Nielsen, M.B. and Marincola, F.M., "Melanoma vaccines: the paradox of T cell activation without clinical response," *Cancer Chemother. Pharmacol.*, 46 (Suppl.): S62-S66 (2000).
Okano, K. et al. "Effects of double blockade of CD28 and inducible costimulator signaling on anti-glomerular basement membrane glomerulonephritis," *J Lab Clin Med*, 144:183-192 (2004).
Pasero, C., et al., "The HVEM network: New directions in targeting novel costimulatory/co-inhibitory molecules for cancer therapy," *Curr. Opin. Immunol.*, 12(4): 478-485 (2012).
PCT/US2010/051008 International Preliminary Report on Patentability, dated Apr. 3, 2012.
PCT/US2010/051008 Transmittal of the International Search Report and the Written Opinion of the International Searching Authority, dated Jun. 16, 2011.
Peggs, K.S., et al., "Principles and Use of Anti-CTLA4 Antibody in Human Cancer Immunotherapy," *Curr. Op. Immun.*, 18(2): 206-213 (2006).
Riley, J.L., et al., "Modulation of TCR-Induced Transcriptional Profiles by Ligation of CD28, ICOS, and CTLA-4 Receptors," *PNAS*, 99(18): 11790-11795 (2002).
Rottman, J.B., et al., "The costimulatory molecule ICOS plays an important role in the immunopathogenesis of EAE," *Nat. Immunol.*, 2(7): 605-611 (2001).
Sakthivel, P., et al., "Attenuation of Immune-Mediated Influenza Pneumonia by Targeting the Inducible C-Stimulator (ICOS) Molecule on T Cells," *PLOS ONE*, 9(7): 1-11 (2014).
Schadendorf, D., et al., "Immunotherapy of distant metastatic disease," *Ann. Oncol.*, 20 Supp. 6, vi41-vi50 (2009).
Sim, G.C., et al., "IL-2 Therapy Promotes Suppressive ICOS$^+$Treg Expansion in Melanoma Patients," *J. Clin. Invest.*, 124(1): 1-12 (2014), downloaded Dec. 9, 2013.
Simpson, T.R., et al., "Regulation of CD4 T Cell Activation and Effector Function by Inducible Costimulator (ICOS)," *Current Opinion in Immunology*, 22: 326-332 (2010).
Smigiel, K.S., et al, "CCR7 Provides Localized Access to IL-2 and Defines Homeostatically Distinct Regulatory T Cell Subsets," *J. Exp. Med.*, 211(1): 121-136 (2014).
Suntharalingam, G., et al., "Cytokine Storm in a Phase 1 Trial of the Anti-CD28 Monoclonal Antibody TGN1412," *N.E. Journal of Medicine*, 355: 1018-1028 (2006).
Swallow, M.M., et al., "B7h, a Novel Costimulatory Homolog of B7.1 and B7.2, Is Induced by TNFα," *Immunity*, 11: 423-432 (1999).
Tajima, N., et al., "Critical role of activation-inducible lymphocyte immunomediatory molecule/inducible costimulator in the effector function of human T cells: a comparative in vitro study of effects of its blockade and CD28 blockade in human beings and monkeys," *Human Immunology*, 69: 399-408 (2008).
Tajima, N., et al., "JTA-009, A Fully Human Antibody Against Human AILIM/ICOS, Ameliorates Graft-Vs-Host Reaction in SCID Mice Grafted with Human PBMCs," *Experimental Hematology*, 36: 1514-1523 (2008).

Tamura, H., et al., "B7-H1 costimulation preferentially enhances CD28-independent T-helper cell function," *Blood*, 97(6): 1809-1816 (2001).
Tang, D.N., et al., "Increased Frequency of ICOS+ CD4 T-Cells as a Pharmacodynamic Biomarker for Anti-Ctla-4 Therapy," *Cancer Immunol. Res.*, 2013.
Tseng, S-Y., et al., "B7-DC, a new dendritic cell molecule with potent cost mulatory properties for T cells," *J. Exp. Med.*, 193(7): 839-845 (2001).
Van Berkel, M.E., et al., "ICOS Contributes to T Cell Expansion in CTLA-4 Deficient Mice," *J. Immunol.*, 175(1):182-188 (2005).
Vesosky, B., et al., "Modulation of Costimulation to Enhance Tumor Immunity," *Cancer Immuno. Immunother.*, 52(11): 663-669 (2003).
Wallin, J.J., et al, "Enhancement of CD8$^+$T cell responses by ICOS/B7h Costimulation," *J. Immuno.*, 167: 132-139 (2001).
Wang, S., et al., "Costimulation of T cells by B7-H2, a B7-like molecule that binds ICOS," *Blood*, 96(8): 2808-2813 (2000).
Wang, S., et al., "Ligand Binding Sites of Inducible Costimulator and High Avidity Mutants with Improved Function," *J. Exp. Med.*, 195 (8): 1033-1041 (2002).
Wang, W., et al., "Biomarkers on Melanoma Patient T Cells Associated with Ipilimumab Treatment," *J. Trans. Med.*, 10(146) (2012).
Ward, R.C. and Kaufman, H.L. "Targeting Costimulatory Pathways for Tumor Immunotherapy," *International Reviews of Immunol.*, 26:161-196 (2007).
Watanabe, M., et al., "A distinct role for ICOS-mediated co-stimulatory signaling in CD4$^+$and CD8$^+$T cell subsets," *Int'l Immuno.*, 17(3): 269-278 (2005).
Winoto, A., and Littman, D.R., "Nuclear hormone receptors in T lymphocytes," *Cell*, 109 Suppl:S57-66 (2002).
Xu, H., et al, "Follicular T-Helper Cell Recruitment Governed by Bystander B Cells and ICOS-Driven Motility," *Nature*, 496: 523-528 (2013).
Yagi, J., et al., "Regulatory Roles of IL-2 and IL-4 in H4 Inducible Costimulator Expression on Activated CD4+ T Cells During Th Cell Development," *J. Immuno.*, 171: 783-794 (2003).
Yao, S., et al., "B7-H2 Is a Costimulatory Ligand for CD28 in Human," *Immunity*, 34(5): 729-740 (2011).
Yoshinaga, S.K., et al., "Characterization of a New Human B7-Related Protein: B7RP-1 is the Ligand to the Co-Stimulatory Protein ICOS," *Int'l Immuno.*, 12(10): 1439-1447 (2000).
Yoshinaga, S.K., et al, "T-cell co-stimulation through B7RP-1 and ICOS," *Nature*, 402: 827-832 (1999).
Zang, X. and Allison, J.P., "The B7 Family and Cancer Therapy: Costimulation and Coinhibition," *Clin. Can. Res.*, 13(18): 5271-5279 (2007).
Zheng, J., et al., "ICOS Regulates the Generation and Function of Human CD4$^+$Treg in a CTLA-4 Dependent Manner," *PLOS ONE*, 8(12): 1-11 (2013).
Zuberek, K., et al., "Comparable in vivo Efficacy of CD28/B7, ICOS/GL50, and ICOS/GL5OB Costimulatory Pathways in Murine Tumor Models: IFNγ-Dependent Enhancement of CTL Priming, Effector Functions, and Tumor Specific Memory CTL," *Cell. Immuno.*, 225: 53-63 (2003).
Ford et al.; "Targeting co-stimulatory pathways: transplantation and autoimmunity;" Nature Reviews Nephrology, vol. 10, Jan. 2014, pp. 14-24.
Keir et al.; "PD-1 and Its Ligands in Tolerance and Immunity;" Annu. Rev. Immunol. (2008), vol. 26; 30 pages.
Brahmer et al.; "Phase II experience with MDX-1106 (Ono-4538), an anti-PD-1 monoclonal antibody, in patients with selected refractory or relapsed malignancies;" *Journal of Clinical Oncology*, 27:15S, May 2009; pp. 3018 (Abstract).
Curran et al.; "PD-1 and CTLA-4 combination blockade expands infiltrating T cells and reduces regulatory T and myeloid cells within B16 melanoma tumors;" *PNAS*, vol. 107, No. 9, Mar. 2, 2010; pp. 4275-4280.
Dranoff et al.; "Vaccination with irradiated tumor cells engineered to secrete murine granulocyte-macrophage colony-stimulating factor stimulates potent, specific, and long-lasting anti-tumor immunity;" *Proc. Natl. Acad. Sci. USA*, vol. 90, Apr. 1993; pp. 3539-3543.

(56) References Cited

OTHER PUBLICATIONS

Overwijk et al.; "B16 as a Mouse Model for Human Melanoma;" *Curr. Protoc. Immunol.* May 2001; Chapter: Unit-20.1; pp. 1-33.
Hirano et al.; "Blockade of B7-H1 and PD-1 by Monoclonal Antibodies Potentiates Cancer Therapeutic Immunity;" *Cancer Research* (Feb. 1, 2005); vol. 65, No. 3; pp. 1089-1096.
Van Elsas et al.; "Combination Immunotherapy of B16 Melanoma Using Anti-Cytotoxic T Lymphocyte—associated Antigen 4 (CTLA-4) and Granulocyte/Macrophage Colony-Stimulating Factor (GM-CSF)-producing Vaccines Induces Rejection of Subcutaneous and Metastatic Tumors Accompanied by Autoimmune Depigmentation;" *J. Exp. Med.*, vol. 190, No. 3, Aug. 2, 1999; pp. 355-366.
Weber et al.; "Phase I/II Study of Ipilimumab for Patients With Metastatic Melanoma;" *Journal of Clinical Oncology*, vol. 26, No. 36, Dec. 20, 2008; pp. 5950-5956.
Zhongbin, D., "Studies on the expression of human ICOS molecule, the preparation of monoclonal antibodies and the biological functions thereof," Chinese Doctoral Dissertations & Master's Theses Full-text Database (Doctor)—Medicine and Health Sciences, E059-40 Jun. 15, 2004.
Iwai, Y. et al., "Involvement of PD-L1 on tumor cells in the escape from host immune system and tumor immunotherapy by PD-L1 blockade", *PNAS*, 99 (19):12293-12297 (2002).
CN 201510169089.9 Notification of First Office Action dated Nov. 30, 2016.
Response to Amendment Under Rule 312 for U.S. Appl. No. 14/250,272, dated May 5, 2016.
Butte et al.; "Programmed Death-1 Ligand 1 Interacts Specifically with the B7-1 Costimulatory Molecule to Inhibit T Cell Responses;" Immunity 27, Jul. 2007; pp. 111-122.
Nemunaitis; "Vaccines in cancer: GVAX®, a GM-CSF gene vaccine;" Expert Rev. Vaccines 4(3), 2005; pp. 259-274.
Notice of Allowance for U.S. Appl. No. 13/498,570, dated Oct. 30, 2013.
Notice of Allowance for U.S. Appl. No. 13/498,570, dated Dec. 10, 2013.
Notice of Allowance for U.S. Appl. No. 14/250,272, dated Feb. 16, 2016.
Office Action for U.S. Appl. No. 13/498,570, dated Mar. 28, 2013.
Office Action for U.S. Appl. No. 14/250,272, dated Sep. 30, 2015.
Third Party Observations and Citations submitted on Nov. 10, 2017, in corresponding EP Application No. 10821297.8, Titled: Combination Immunotherapy for the Treatment of Cancer.
Third Party Observations and Citations submitted on Nov. 22, 2017, in corresponding EP Application No. 10821297.8, Titled: Combination Immunotherapy for the Treatment of Cancer.
Communication Pursuant to Article 94(3) EPC for European Application No. EP10821297.8, titled: Combination Immunotherapy for the Treatment of Cancer, Dated: Oct. 12, 2015.
Summons to Attend Oral Proceedings Pursuant to Rule 115(1) EPC for European Application No. EP10821297.8, titled: Combination Immunotherapy for the Treatment of Cancer, Dated: Apr. 12, 2017.
Annex to Summons to Attend Oral Proceedings Pursuant to Rule 115(1) EPC for European Application No. EP10821297.8, titled: Combination Immunotherapy for the Treatment of Cancer, Dated: Apr. 12, 2017.
Written Submissions in Response to Summons to Oral Proceedings for European Application No. EP10821297.8, titled: Combination Immunotherapy for the Treatment of Cancer, Dated: Oct. 31, 2017.
Accompanying Documents to Written Submissions in Response to Summons to Oral Proceedings for European Application No. EP10821297.8, titled: Combination Immunotherapy for the Treatment of Cancer, Dated: Oct. 31, 2017.
Comments by the Examining Division on the Observations by a Third Party for European Application No. EP10821297.8, titled: Combination Immunotherapy for the Treatment of Cancer, Dated: Nov. 17, 2017.
Communication Under Rule 71(3) EPC for European Application No. EP10821297.8, titled: Combination Immunotherapy for the Treatment of Cancer, Dated: Dec. 15, 2017.

* cited by examiner

COMBINATION IMMUNOTHERAPY FOR THE TREATMENT OF CANCER

RELATED APPLICATIONS

This application is a divisional of U.S. application Ser. No. 14/250,272, filed on Apr. 10, 2014, which is a divisional of U.S. application Ser. No. 13/498,570, filed on Sep. 30, 2010, now U.S. Pat. No. 8,709,417, which is the U.S. National Stage of International Application No. PCT/US2010/051008, filed on Sep. 30, 2010, published in English, which claims the benefit of U.S. Provisional Application No. 61/247,438, filed on Sep. 30, 2009. The entire teachings of U.S. application Ser. No. 14/250,272 are incorporated herein by reference.

FIELD OF THE INVENTION

The present invention relates generally to methods and compositions for the treatment of cancer employing T cell inhibitory receptor blockade in conjunction with ICOS stimulation.

BACKGROUND OF THE INVENTION

Optimal T cell activation requires contemporaneous signals through the T cell receptor and costimulatory molecules. CD28, the prototypical costimulatory molecule, upon interaction with its ligands B7-1 and B7-2, plays a crucial role in initial T cell priming. Sharpe et al., *Nat. Rev. Immunol.* 2:203-209 (2002). CD28-mediated T cell expansion is opposed by another B7-1,2 counter receptor, cytotoxic T lymphocyte associated antigen 4 (CTLA-4), which attenuates the proliferation of recently activated T cells. Krummel et al., *J. Exp. Med.* 183:2533-2540 (1996); Leach et al., *Science* 271:1734-1736 (1996). Temporal regulation of CD28 and CTLA-4 expression maintains a balance between activating and inhibitory signals and ensures the development of an effective immune response, while safeguarding against the development of autoimmunity. Blockade of the inhibitory signals mediated by CTLA-4 has been shown to enhance T cell responses and induce tumor rejection in a number of animal models, and monoclonal antibodies to human CTLA-4 have found modest success in ongoing human clinical trials, including durable complete responses in a small subset of patients with metastatic disease. See, e.g. Korman et al, *Adv. Immunol.* 90:297-339 (2006).

The identification and characterization of additional CD28 and B7 family members PD-1 (programmed death-1), PD-L1 (programmed death ligand-1 or B7-H1), and PD-L2 (B7-DC) has added further complexity to the process of T-cell activation and peripheral tolerance in humans. Similar to the B7-1,2/CTLA-4 interaction, PD-1 interactions with PD-L1 and PD-L2 downregulate central and peripheral immune responses. Fife et al., *Immunol. Rev.* 224:166-82 (2008). Accordingly, antibody-based blockade of PD-1, like CTLA-4, is also being explored in human clinical trials for the treatment of cancer. See, e.g., Berger et al. *Clin. Cancer Res.* 14:3044-3051 (2008). Nevertheless, as with CTLA-4, improved therapies are still needed.

Inducible costimulator (ICOS) is a T-cell-specific surface molecule that is structurally related to CD28 and CTLA-4. Hutloff et al., *Nature* 397:263-266 (1999); Dong et al., *Nature* 409:97-101 (2001). Initially, the role of ICOS in immune responses was strongly linked to the production of Th2 cytokines, suggesting that ICOS-expressing T cells might play a role in suppressing immune responses. ICOS-deficient mice demonstrated decreased production of the Th2 cytokine interleukin 10, and IL-10 production by regulatory T cells has been associated with the suppression of effector T cell responses in a cell-extrinsic manner. Yoshinaga et al., *Nature* 402:827-832 (1999); Kohyama et al., *Proc. Natl. Acad. Sci. USA* 101:4192-97 (2004). Contrarily, however, more recent data suggested that ICOS-expressing T cells might also be involved in autoimmune responses, and CTLA-4 blockade in bladder cancer patients was shown to increase ICOS expression on CD4+ T cells, which cells then produced IFN-gamma and recognized tumor antigen. Yu et al. *Nature* 450:299-303 (2007); Liakou et al., *Proc. Natl. Acad. Sci. USA* 105:14987-992 (2008). Further, ICOS has also been shown to be associated with increased survival of both effector memory and regulatory T cells, demonstrating that its functional relevance may not be restricted to regulatory T cells. Burmeister et al., *J. Immunol.* 180:774-782 (2008). As such, the physiological role of ICOS signaling in the T cell activation process is still being unraveled. Due to this continuing uncertainty, the potential impact of modulating ICOS signaling in the context of cancer therapy is currently unknown.

SUMMARY OF INVENTION

The present invention clarifies the role of ICOS signaling in the progression or treatment of cancer by demonstrating that the contemporaneous administration of an ICOS agonist in conjunction with T cell inhibitory receptor blockade can further enhance the anti-tumor effects of the blockade. Accordingly, compositions and methods are provided combining the blockade of a T cell inhibitory receptor (e.g., CTLA-4 and/or PD-1) with agonist-induced ICOS signaling for the treatment of cancer. Function-activating ICOS antibodies are provided as well as ICOS-Ligand-expressing vaccines for use in the subject compositions and methods.

DETAILED DESCRIPTION

Figure 1:
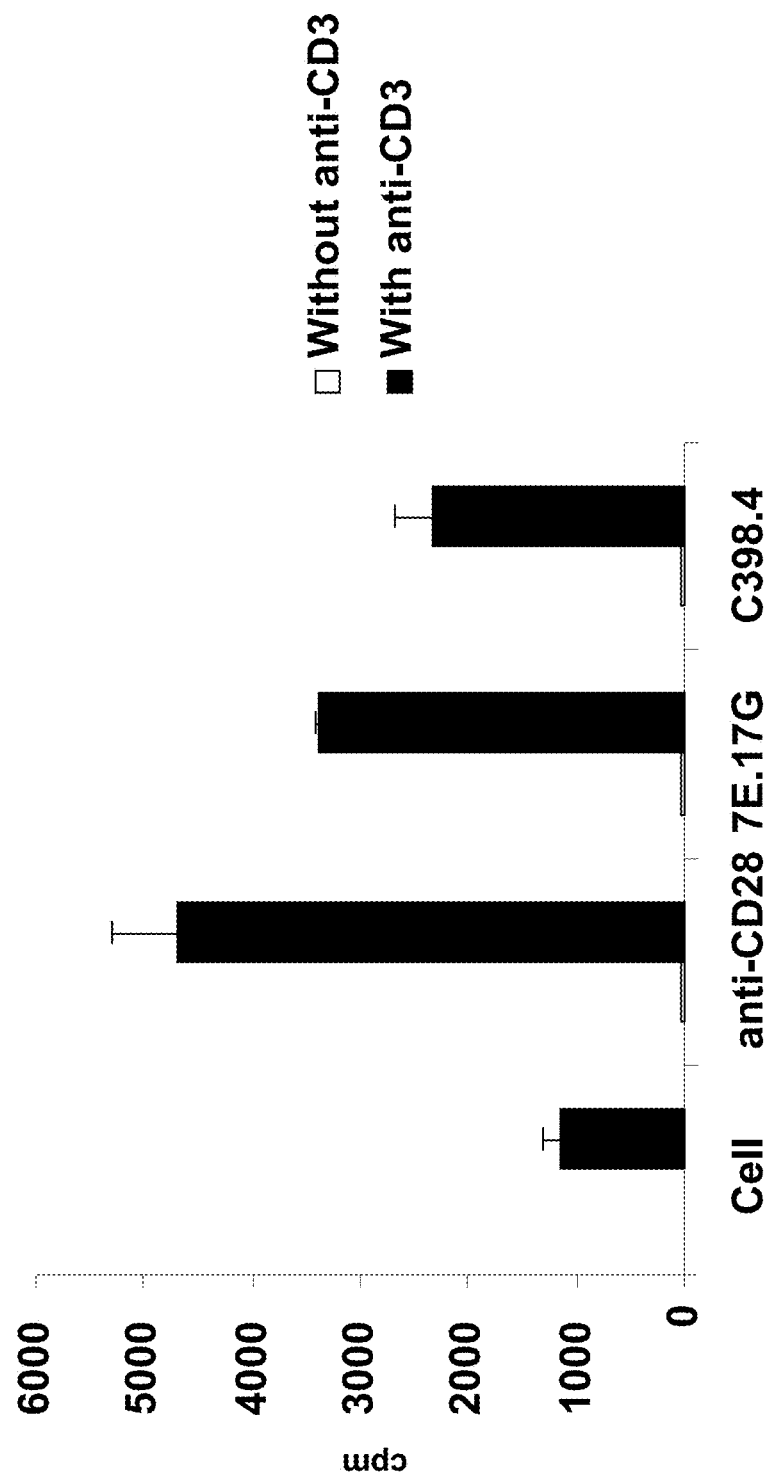
FIG. 1 shows the agonistic effect of anti-ICOS antibody (7E. 17G or C398.4) on murine CD4$^+$ T cells in the absence or presence of anti-CD3 antibody.

Described herein is the finding that stimulation of ICOS-mediated signaling, e.g., via ICOS ligand or an agonist antibody, enhances the anti-tumor effects of blocking agents to T cell inhibitory receptors such as CTLA-4 and PD-1. Accordingly, provided herein are compositions comprising a blocking agent to a T cell inhibitory receptor and an ICOS stimulating agent, and methods of using such compositions to treat a patient afflicted with cancer.

Blocking Agents to T Cell Inhibitory Receptors/Stimulating Agents to ICOS

Inducible T cell co-stimulator (ICOS) is also known as "AILIM," "CD278," and "MGC39850". The complete cDNA sequence of ICOS has the GENBANK accession number of NM_012092.3 and the amino acid sequence of human ICOS has GENBANK accession number of NP_036224. ICOS belongs to the CD28 and CTLA-4 cell-surface receptor family. It forms homodimers and plays an important role in cell-cell signaling, immune responses, and regulation of cell proliferation. However, the role of ICOS signaling in mediating anti-tumor responses is currently unknown.

An ICOS ligand (ICOSL) is also referred to as "B7H2," "GL50," "B7-H2," "B7RP1," "CD275," "ICOSLG," "LICOS," "B7RP-1," "ICOS-L", and "KIAA0653." The complete cDNA sequence of ICOSL has the GENBANK accession number of NM_015259.4 and the amino acid sequence of human ICOSL has the GENBANK accession number of NP_056074.

Stimulating agents to ICOS are molecules that generally bind to the extracellular domain of ICOS (e.g., ICOSL). Usually the binding affinity of the blocking agent will be at least about 100 μM. The stimulating agent will be substantially unreactive with related molecules to ICOS, such as CD28 and other members of the immunoglobulin superfamily. As demonstrated herein, suitable stimulating agents activate signaling of ICOS and result in a corresponding increase in T cell activation (e.g., proliferation). See, e.g. FIG. 1.

Candidate ICOS stimulating agents are screened for their ability to meet this criteria. Assays to determine affinity and specificity of binding are known in the art, including competitive and non-competitive assays. Assays of interest include ELISA, RIA, flow cytometry, etc. Binding assays may use purified or semi-purified ICOS, or alternatively may use T cells that express ICOS, e.g. cells transfected with an expression construct for ICOS; T cells that have been stimulated through cross-linking of CD3 and CD28; the addition of irradiated allogeneic cells, etc. As an example of a binding assay, purified ICOS may be bound to an insoluble support, e.g. microtiter plate, magnetic beads, etc. The candidate stimulating agent and soluble, labeled ICOS ligand are added to the cells, and the unbound components are then washed off. The ability of the stimulating agent to compete with the natural ligand for ICOS binding may be determined by quantitation of bound, labeled ligand.

A functional assay that detects T cell activation may be used for confirmation that the agent is a stimulating agent of ICOS. For example, a population of T cells may be stimulated with the candidate stimulating agent in the presence and absence of anti-CD3, as exemplified herein and in FIG. 1. An agent that stimulates ICOS will cause an increase in the T cell activation, as measured by, e.g. CD4+ T cell proliferation and/or cell cycle progression, release of IL-2, upregulation of CD25 and CD69, etc. It will be understood by one of skill in the art that expression on the surface of a cell, packaging in a liposome, adherence to a particle or well, etc. will increase the effective valency of a molecule.

A T cell inhibitory receptor as used herein includes any receptor expressed on the surface of T cells which, when activated or bound by ligand, downregulates activation of the T cell. In other words, blocking the T cell inhibitory receptor enhances T cell activation and/or effector T cell responses. T cell inhibitory receptors and their ligands are well-known in the art. Non-limiting and exemplary T cell inhibitory receptors include CTLA-4 and PD-1. An skilled artisan will recognize that the ligands for CTLA-4 include CD80 and CD86. Further, a skilled artisan will recognize that the ligands for PD-1 include PD-L1 and PD-L2.

The complete cDNA sequence of human CTLA-4 has the GENBANK accession number L15006. The region of amino acids 1-37 is the leader peptide; 38-161 is the extracellular V-like domain; 162-187 is the transmembrane domain; and 188-223 is the cytoplasmic domain. Variants of the nucleotide sequence have been reported, including a G to A transition at position 49, a C to T transition at position 272, and an A to G transition at position 439. The complete DNA sequence of mouse CTLA-4 has the EMBL accession number X05719 (Brunet et al. (1987) Nature 328:267-270). The region of amino acids 1-35 is the leader peptide.

The complete cDNA sequence of human PD-1 has the GENBANK accession number NM_005018 and the amino acid sequence of human PD-1 has GENBANK accession number NP_005009.1. The region of amino acids 1-20 is the signal peptide, and the mature peptide is found at amino acids 21-288.

Blocking agents to a T cell inhibitory receptor are generally molecules that specifically bind to the extracellular domain the T cell inhibitory receptor or the extracellular domain of the T cell inhibitory receptor ligand to prevent activation of the T cell inhibitory receptor, e.g., by blocking the binding of the T cell inhibitory receptor to its ligand, e.g. CD80, CD86, PD-L1, PD-L2, etc. Usually the binding affinity of the blocking agent will be at least about 100 μM. The blocking agent will be substantially unreactive with related molecules to the T cell inhibitory receptor, such as CD28 and other members of the immunoglobulin superfamily. Further, blocking agents do not activate signaling of the T cell inhibitory receptor. Conveniently, this is achieved by the use of monovalent or bivalent binding molecules. It will be understood by one of skill in the art that the following discussions of cross-reactivity and competition between different molecules is intended to refer to molecules having the same species of origin, e.g. human T cell inhibitory receptor binds human T cell inhibitory receptor ligand, etc.

Candidate blocking agents are screened for their ability to meet this criteria. Assays to determine affinity and specificity of binding are known in the art, including competitive and non-competitive assays. Assays of interest include ELISA, RIA, flow cytometry, etc. Binding assays may use purified or semi-purified T cell inhibitory receptor protein, or alternatively may use T cells that express the T cell inhibitory receptor, e.g. cells transfected with an expression construct for the T cell inhibitory receptor; T cells that have been stimulated through cross-linking of CD3 and CD28; the addition of irradiated allogeneic cells, etc. As an example of a binding assay, purified T cell inhibitory receptor protein is bound to an insoluble support, e.g. microtiter plate, magnetic beads, etc. The candidate blocking agent and soluble, labeled T cell inhibitory receptor ligand are added to the cells, and the unbound components are then washed off. The ability of the blocking agent to compete with the ligand for T cell inhibitory receptor binding is determined by quantitation of bound, labeled ligand.

Generally, a soluble monovalent or bivalent binding molecule will not activate T cell inhibitory receptor signaling. A functional assay that detects T cell activation may be used for confirmation. For example, a population of T cells may be stimulated with irradiated allogeneic cells expressing the T cell inhibitory receptor ligand, in the presence or absence of the candidate blocking agent. An agent that blocks T cell inhibitory receptor signaling will cause an increase in the T cell activation, as measured by proliferation and cell cycle progression, release of IL-2, upregulation of CD25 and CD69, etc. It will be understood by one of skill in the art that expression on the surface of a cell, packaging in a liposome, adherence to a particle or well, etc. will increase the effective valency of a molecule.

A blocking agent to a T cell inhibitory receptor or a stimulating agent to ICOS may each individually be a peptide, small organic molecule, peptidomimetic, soluble ligands, antibody, or the like. Antibodies are a preferred blocking agent or stimulating agent. Antibodies may be polyclonal or monoclonal; intact or truncated, e.g. F(ab')$_2$, Fab, Fv; xenogeneic, allogeneic, syngeneic, or modified forms thereof, e.g. humanized, chimeric, etc.

In many cases, the blocking agent to a T cell inhibitory receptor or stimulating agent to ICOS will be an oligopeptide, e.g. antibody or fragment thereof, etc., but other molecules that provide relatively high specificity and affinity may also be employed. Combinatorial libraries provide compounds other than oligopeptides that have the necessary binding characteristics. Generally, the affinity will be at least about $10^{-6}$, more usually about $10^{-8}$M, i.e. binding affinities normally observed with specific monoclonal antibodies.

A number of screening assays are available for blocking agents to a T cell inhibitory receptor or stimulating agents to ICOS. The components of such assays will typically include the T cell inhibitory receptor (and optionally a T cell inhibitory receptor activating agent, e.g. the T cell inhibitory receptor ligand) or ICOS, respectively. The assay mixture will also comprise a candidate pharmacological agent. Generally a plurality of assay mixtures are run in parallel with different agent concentrations to obtain a differential response to the various concentrations. Typically, one of these concentrations serves as a negative control, i.e. at zero concentration or below the level of detection.

Conveniently, in these assays one or more of the molecules will be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule which provides for detection, in accordance with known procedures.

One screening assay of interest is directed to agents that either interfere with the activation of a T cell inhibitory receptor by its cognate ligands(s) or that activate ICOS signaling. Quantitation of activation may achieved by a number of methods known in the art. For example, T cell activation may be determined by quantitating cell proliferation, release of cytokines, etc.

Other assays of interest are directed to agents that block the binding of the T cell inhibitory receptor to its counter-receptor(s) or ligand. The assay mixture will comprise at least a portion of the natural counter-receptor, or an oligopeptide that shares sufficient sequence similarity to provide specific binding, and the candidate pharmacological agent. The oligopeptide may be of any length amenable to the assay conditions and requirements, usually at least about 8 aa in length, and up to the full-length protein or fusion thereof. The T cell inhibitory receptor may be bound to an insoluble substrate. The substrate may be made in a wide variety of materials and shapes e.g. microtiter plate, microbead, dipstick, resin particle, etc. The substrate is chosen to minimize background and maximize signal to noise ratio. Binding may be quantitated by a variety of methods known in the art. After an incubation period sufficient to allow the binding to reach equilibrium, the insoluble support is washed, and the remaining label quantitated. Agents that interfere with binding will decrease the detected label.

Candidate blocking or stimulating agents encompass numerous chemical classes, though typically they are organic molecules, preferably small organic compounds having a molecular weight of more than 50 and less than about 2,500 daltons. Candidate blocking or stimulating agents comprise functional groups necessary for structural interaction with proteins, particularly hydrogen bonding, and typically include at least an amine, carbonyl, hydroxyl, sulfhydryl or carboxyl group, preferably at least two of the functional chemical groups. The candidate blocking or stimulating agents often comprise cyclical carbon or heterocyclic structures and/or aromatic or polyaromatic structures substituted with one or more of the above functional groups. Candidate blocking or stimulating agents are also found among biomolecules including peptides, saccharides, fatty acids, steroids, purines, pyrimidines, derivatives, structural analogs or combinations thereof.

Candidate blocking or stimulating agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

A variety of other reagents may be included in the screening assay. These include reagents like salts, neutral proteins, e.g. albumin, detergents, etc which may be used to facilitate optimal protein-DNA binding and/or reduce non-specific or background interactions. Also reagents that otherwise improve the efficiency of the assay, such as protease inhibitors, nuclease inhibitors, anti-microbial agents, etc. may be used.

Suitable antibodies for use as blocking agents or stimulating agents may be obtained by immunizing a host animal with peptides comprising all or a portion of the T cell inhibitory receptor or ICOS protein, respectively. Suitable host animals include mouse, rat sheep, goat, hamster, rabbit, etc. The origin of the protein immunogen may be mouse, human, rat, monkey etc. The host animal will generally be a different species than the immunogen, e.g. mouse T cell inhibitory receptor used to immunize hamsters, human T cell inhibitory receptor to immunize mice, etc. The human and mouse T cell inhibitory receptor contain highly conserved stretches in the extracellular domain (Harper et al. (1991) J. Immunol. 147:1037-1044). Peptides derived from such highly conserved regions may be used as immunogens to generate cross-specific antibodies.

The immunogen may comprise the complete protein, or fragments and derivatives thereof. Preferred immunogens comprise all or a part of the extracellular domain of human T cell inhibitory receptor (e.g., amino acid residues 38-161 of human CTLA-4) or ICOS protein, where these residues contain the post-translation modifications, such as glycosylation, found on the native T cell inhibitory receptor. Immunogens comprising the extracellular domain are produced in a variety of ways known in the art, e.g. expression of cloned genes using conventional recombinant methods, isolation from T cells, sorted cell populations expressing high levels of the immunogen, etc.

Where expression of a recombinant or modified protein is desired for production of an immunogen, a vector encoding the desired portion of the T cell inhibitory receptor or ICOS protein will be used. Generally, an expression vector will be designed so that the extracellular domain of the T cell inhibitory receptor or ICOS protein is on the surface of a transfected cell, or alternatively, the extracellular domain is secreted from the cell. When the extracellular domain is to be secreted, the coding sequence for the extracellular domain will be fused, in frame, with sequences that permit secretion, including a signal peptide. Signal peptides may be exogenous or native. A fusion protein of interest for immunization joins the extracellular domain of the T cell inhibitory receptor to the constant region of an immunoglobulin. For example, a fusion protein comprising the extracellular domain of a murine T cell inhibitory receptor or ICOS protein joined to the hinge region of human Cg1 (hinge-CH2-CH3) domain may be used to immunize hamsters.

When the T cell inhibitory receptor or ICOS protein immunogen is to be expressed on the surface of the cell, the coding sequence for the extracellular domain will be fused, in frame, with sequences encoding a peptide that anchors the extracellular domain into the membrane and a signal sequence. Such anchor sequences include the native T cell inhibitory receptor or ICOS protein transmembrane domain, or transmembrane domains from other cell surface proteins, e.g. CD4, CD8, sIg, etc. Mouse cells transfected with the human T cell inhibitory receptor gene or the human ICOS gene may be used to immunize mice and generate antibodies specific for the human T cell inhibitory receptor protein or ICOS protein, respectively.

Monoclonal antibodies are produced by conventional techniques. Generally, the spleen and/or lymph nodes of an immunized host animal provide a source of plasma cells. The plasma cells are immortalized by fusion with myeloma cells to produce hybridoma cells. Culture supernatant from individual hybridomas is screened using standard techniques to identify those producing antibodies with the desired specificity. Suitable animals for production of monoclonal antibodies to the human protein include mouse, rat, hamster, etc. To raise antibodies against the mouse protein, the animal will generally be a hamster, guinea pig, rabbit, etc. The antibody may be purified from the hybridoma cell supernatants or ascites fluid by conventional techniques, e.g. affinity chromatography using the T cell inhibitory receptor bound to an insoluble support, protein A sepharose, etc.

The antibody may be produced as a single chain, instead of the normal multimeric structure. Single chain antibodies are described in Jost et al. (1994) J.B.C. 269:26267-73, and others. DNA sequences encoding the variable region of the heavy chain and the variable region of the light chain are ligated to a spacer encoding at least about 4 amino acids of small neutral amino acids, including glycine and/or serine. The protein encoded by this fusion allows assembly of a functional variable region that retains the specificity and affinity of the original antibody.

For in vivo use, particularly for injection into humans, it is desirable to decrease the antigenicity of the blocking agent or stimulating agent. An immune response of a recipient against the blocking agent will potentially decrease the period of time that the therapy is effective. Methods of humanizing antibodies are known in the art. The humanized antibody may be the product of an animal having transgenic human immunoglobulin constant region genes (see for example International Patent Applications WO 90/10077 and WO 90/04036). Alternatively, the antibody of interest may be engineered by recombinant DNA techniques to substitute the CH1, CH2, CH3, hinge domains, and/or the framework domain with the corresponding human sequence (see WO 92/02190).

The use of Ig cDNA for construction of chimeric immunoglobulin genes is known in the art (Liu et al. (1987) P.N.A.S. 84:3439 and (1987) J. Immunol. 139:3521). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al. (1991) Sequences of Proteins of Immunological Interest, N.I.H. publication no. 91-3242. Human C region genes are readily available from known clones. The choice of isotype will be guided by the desired effector functions, such as complement fixation, or activity in antibody-dependent cellular cytotoxicity. Preferred isotypes are IgG1, IgG3 and IgG4. Either of the human light chain constant regions, kappa or lambda, may be used. The chimeric, humanized antibody is then expressed by conventional methods.

Antibody fragments, such as Fv, F(ab').sub.2 and Fab may be prepared by cleavage of the intact protein, e.g. by protease or chemical cleavage. Alternatively, a truncated gene is designed. For example, a chimeric gene encoding a portion of the F(ab').sub.2 fragment would include DNA sequences encoding the CH1 domain and hinge region of the H chain, followed by a translational stop codon to yield the truncated molecule.

Consensus sequences of H and L J regions may be used to design oligonucleotides for use as primers to introduce useful restriction sites into the J region for subsequent linkage of V region segments to human C region segments. C region cDNA can be modified by site directed mutagenesis to place a restriction site at the analogous position in the human sequence.

Expression vectors include plasmids, retroviruses, YACs, EBV derived episomes, and the like. A convenient vector is one that encodes a functionally complete human CH or CL immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting chimeric antibody may be joined to any strong promoter, including retroviral LTRs, e.g. SV-40 early promoter, (Okayama et al. (1983) Mol. Cell. Bio. 3:280), Rous sarcoma virus LTR (Gorman et al. (1982) P.N.A.S. 79:6777), and moloney murine leukemia virus LTR (Grosschedl et al. (1985) Cell 41:885); native Ig promoters, etc.

In one embodiment, the blocking agent to a T cell inhibitory receptor is an anti-CTLA-4 antibody that binds to the extracellular domain of CTLA-4 and inhibits anti-CTLA-4 signaling. Suitable anti-CTLA-4 antibodies for use in humans include, e.g., ipilimumab (MDX-010) and tremelimumab (CP 675,206). In another embodiment, the blocking agent to a T cell inhibitory receptor is an anti-PD-1 antibody that blocks binding of PD-1 to PD-L1 and inhibits PD-1 signaling. Suitable antibodies for use in humans include, e.g., MDX-1106/ONO-4538 and CT-011. In another embodiment, the blocking agent to a T cell inhibitory receptor is an anti-B7-H1 (PD-1L) antibody that blocks binding of PD-1 to PD-1L and inhibits PD-1 signaling. In another embodiment, the blocking agent to a T cell inhibitory agent is a combination of an anti-CTLA-4 antibody and/or an anti-PD-1 antibody and/or an anti-B7-H1 antibody.

In another embodiment, stimulating agent to ICOS is an anti-ICOS antibody that binds to the extracellular domain of ICOS and activates ICOS signaling, which leads to an increase in T cell activation, e.g., proliferation. In another embodiment, the stimulating agent to ICOS is recombinant ICOSL, which may be soluble or expressed on the surface of a genetically modified cell.

Viral Vectors Encoding Blocking or Stimulating Agents and Cells Expressing Same

In one embodiment, the blocking agent(s) to one or more T cell inhibitory receptors and/or the stimulating agent to ICOS is expressed by viral vectors and transformed cells. For example, the viral vectors and transformed human cells described herein may express anti-T cell inhibitory receptor antibodies to block signaling by the T cell inhibitory receptor and/or a stimulating agent to ICOS (e.g., ICOS ligand) that activates ICOS mediated signaling. In a preferred embodiment, the viral vector or human cells expressing the candidate blocking and/or stimulating agent(s) are capable of expressing the agent(s) proximal to a tumor, particularly a tumor infiltrating lymphocyte.

Human cells that can be used include tumor cells, antigen-presenting cells (e.g. dendritic cells), B cells and T cells. The presently disclosed cells provide for localized expression of the blocking and/or stimulating agent(s) by cells proximal to a tumor. The cells can be modified in vivo, or alternatively cells modified ex vivo can be administered to a patient by a variety of methods, such as by injection.

In one embodiment, the cell is a tumor cell. For ex vivo transformation, such tumor cells can be irradiated to eliminate the ability of the cell to replicate, as known in the art, while maintaining the transient expression of the blocking and/or stimulating agent(s) after administration. For in vivo transformation, non-integrative expression vectors may be preferred.

In certain preferred embodiments, the tumor cell is autologous or endogenous. In the former instance, the tumor cell is taken from a patient, transfected or transduced with a construct encoding the blocking and/or stimulating agent(s) and re-introduced to the patient, for example after irradiation. In the latter instance, the tumor cell is transformed in vivo by local administration of an appropriate construct as described herein.

In an alternative embodiment, the modified tumor cell is allogeneic. The allogeneic tumor cell thus can be maintained in a cell line. In this instance, the tumor cell can be selected from the cell line, irradiated, and introduced to the patent.

In another alternative embodiment, the modified human cells are antigen-presenting cells such as dendritic cells, or monocytes. In another alternative embodiment, the modified human cells are T cells.

Modified human cells capable of producing the blocking and/or stimulating agent(s) can be made by transfecting or transducing the cells with an expression vector encoding the blocking and/or stimulating agent(s). Expression vectors for the expression of a blocking agent, a stimulating agent, or a combination of blocking agent(s) and/or stimulating agents can be made by methods well known in the art.

In various embodiments, the blocking and/or stimulating agent(s) can be administered to a patient in the form of one or more nucleic acid construct.

In one embodiment, the construct comprises a retroviral vector. Retroviral vectors are capable of permanently integrating DNA encoding the blocking and/or stimulating agent(s) into the cell genome. Thus, in the case of ex vivo manipulation of autologous or allogeneic cells, stable cell lines that constitutively produce the blocking and/or stimulating agent(s) can be prepared. In a preferred embodiment, the cells are irradiated prior to administration to a patient. The irradiated cells produce the blocking and/or stimulating agent(s) for a limited period of time In one embodiment, the expression construct comprises an SFV vector, which demonstrates high levels of transient expression in mammalian cells. The SFV vector is described, for example, in Lundstrom, Expert Opin. Biol. Ther. 3:771-777 (2003), incorporated herein by reference in its entirety. Thus, in the case of in vivo manipulation of endogenous cells in a patient, transient expression of high levels of the blocking and/or stimulating agent(s) can be accomplished. This is to prevent constitutive expression, and permanent activation, of T cells in vivo.

Systems capable of expressing recombinant protein in vivo are known in the art. By way of example and not limitation, the system can use the 2A mediated antibody expression system disclosed in Fang et al., Nature Biotech. 23(5) 2005 and U.S. Patent Publication 2005/0003506, the disclosures of which are expressly incorporated by reference herein in their entirety. Other systems known in the art are contemplated, and can also be adapted to produce blocking and/or stimulating agent(s) in vivo as described herein.

Administration of the blocking and/or stimulating agent expressing cells disclosed herein can be combined with administration of cytokines that stimulate antigen-presenting cells such as granulocyte-macrophage colony stimulating factor (GM-CSF)1 macrophage colony stimulating factor (M-CSF), granulocyte colony stimulating factor (G-CSF), interleukin 3 (IL-3), interleukin 12 (IL-12), etc., or cellular vaccines capable of expressing such cytokines. In preferred embodiments, the blocking and/or stimulating agent(s) expressing cells are further modified to express such cytokines. Additional proteins and/or cytokines known to enhance T cell proliferation and secretion, such as IL-1, IL-2, B7, anti-CD3 and anti-CD28 can be employed simultaneously or sequentially with the blocking agents to augment the immune response. The present therapy can also be combined with any of the molecules, or conducted as described in, U.S. Pat. No. 6,051,227, incorporated herein by reference in its entirety.

Vectors and Methods of Transformation

Expression vectors encoding the blocking and/or stimulating agent(s) may be viral or non-viral. Viral vectors are preferred for use in vivo. Expression vectors of the invention comprise an nucleic acid encoding a blocking agent to a T cell inhibitory receptor or a nucleic acid encoding a stimulating agent to ICOS, or a complement thereof, operably linked to an expression control region, or complement thereof, that is functional in a mammalian cell. The expression control region is capable of driving expression of the operably linked blocking and/or stimulating agent encoding nucleic acid such that the blocking and/or stimulating agent is produced in a human cell transformed with the expression vector.

Expression control regions are regulatory polynucleotides (sometimes referred to herein as elements), such as promoters and enhancers, that influence expression of an operably linked nucleic acid.

An expression control region of an expression vector of the invention is capable of expressing operably linked encoding nucleic acid in a human cell. In one embodiment, the cell is a tumor cell. In one embodiment, the cell is a non-tumor cell.

In one embodiment, the expression control region confers regulatable expression to an operably linked nucleic acid. A signal (sometimes referred to as a stimulus) can increase or decrease expression of a nucleic acid operably linked to such an expression control region. Such expression control regions that increase expression in response to a signal are often referred to as inducible. Such expression control regions that decrease expression in response to a signal are often referred to as repressible. Typically, the amount of increase or decrease conferred by such elements is proportional to the amount of signal present; the greater the amount of signal, the greater the increase or decrease in expression.

Especially preferred for use in the present invention are inducible promoters capable of effecting high level of expression transiently in response to a cue. When in the proximity of a tumor cell, a cell transformed with an expression vector for the blocking and/or stimulating agent(s) comprising such an expression control sequence is induced to transiently produce a high level of ICOS ligand by exposing the transformed cell to an appropriate cue.

Preferred inducible expression control regions include those comprising an inducible promoter that is stimulated with a cue such as a small molecule chemical compound. Particular examples can be found, for example, in U.S. Pat. Nos. 5,989,910, 5,935,934, 6,015,709, and 6,004,941, each of which is incorporated herein by reference in its entirety.

Expression control regions include full-length promoter sequences, such as native promoter and enhancer elements, as well as subsequences or polynucleotide variants which retain all or part of full-length or non-variant function. As used herein, the term "functional" and grammatical variants thereof, when used in reference to a nucleic acid sequence, • subsequence or fragment, means that the sequence has one or more functions of native nucleic acid sequence (e.g., non-variant or unmodified sequence).

As used herein, "operable linkage" refers to a physical juxtaposition of the components so described as to permit them to function in their intended manner. In the example of an expression control element in operable linkage with a nucleic acid, the relationship is such that the control element modulates expression of the nucleic acid. Typically, an expression control region that modulates transcription is juxtaposed near the 5' end of the transcribed nucleic acid (i.e., "upstream"). Expression control regions can also be located at the 31 end of the transcribed sequence (i.e., "downstream") or within the transcript (e.g., in an intron). Expression control elements can be located at a distance away from the transcribed sequence (e.g., 100 to 500, 500 to 1000, 2000 to 5000, or more nucleotides from the nucleic acid). A specific example of an expression control element is a promoter, which is usually located 5' of the transcribed sequence. Another example of an expression control element is an enhancer, which can be located 5' or 3' of the transcribed sequence, or within the transcribed sequence.

Expression systems functional in human cells are well known in the art, and include viral systems. Generally, a promoter functional in a human cell is any DNA sequence capable of binding mammalian RNA polymerase and initiating the downstream (3') transcription of an ICOS ligand coding sequence into mRNA. A promoter will have a transcription initiating region, which is usually placed proximal to the 5' end of the coding sequence, and typically a TATA box located 25-30 base pairs upstream of the transcription initiation site. The TATA box is thought to direct RNA polymerase II to begin RNA synthesis at the correct site. A promoter will also typically contain an upstream promoter element (enhancer element), typically located within 100 to 200 base pairs upstream of the TATA box. An upstream promoter element determines the rate at which transcription is initiated and can act in either orientation. Of particular use as promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Typically, transcription termination and polyadenylation sequences recognized by mammalian cells are regulatory regions located 3' to the translation stop codon and thus, together with the promoter elements, flank the coding sequence. The 31 terminus of the mature mRNA is formed by site-specific post-translattonal cleavage and polyadenylation. Examples of transcription terminator and polyadenylation signals include those derived from SV40. lntrons may also be included in expression constructs.

There are a variety of techniques available for introducing nucleic acids into viable cells. Techniques suitable for the transfer of nucleic acid into mammalian cells in vitro include the use of liposomes, electroporation, microinjection, cell fusion, polymer-based systems, DEAE-dextran, viral transduction, the calcium phosphate precipitation method, etc. For in vivo gene transfer, a number of techniques and reagents may also be used, including liposomes; natural polymer-based delivery vehicles, such as chitosan and gelatin; viral vectors are also preferred for in vivo transduction (e.g., Dzau et al., Trends in Biotechnology 11, 205-210 [1993]). In some situations it is desirable to provide a targeting agent, such as an antibody or ligand specific for a tumor cell surface membrane protein. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., J. Biol. Chem. 262, 4429-4432 (1987); and Wagner et al., Proc. Natl. Acad. Sci. USA 87, 3410-3414 (1990). For review of gene therapy protocols see Anderson et al., Science 256, 808-813 (1992).

Where appropriate, gene delivery agents such as, e.g. integration sequences can also be employed. Numerous integration sequences are known in the art (see for example Nunes-Duby et al., Nucleic Acids Res. 26:391-406, 1998; Sadwoski, J. Bacteriol., 165:341-357, 1986; Bestor, Cell, 122(3):322-325, 2005; Plasterk et al., TIG 15:326-332, 1999; Kootstra et al., Ann. Rev. Pharm. Toxicol., 43:413-439, 2003). These include recombinases and transposases. Examples include Cre (Sternberg and Hamilton, J. Mol. Biol., 150:467-486, 1981), lambda (Nash, Nature, 247, 543-545, 1974), Flp (Broach, et al, Cell, 29:227-234, 1982) R (Matsuzaki, et al, J. Bacteriology, 172:610-618, 1990), φC31 (see for example Groth et al., J. Mol. Biol. 335:667-678, 2004), sleeping beauty, transposases of the mariner family (Plasterk et al., supra), and components for integrating viruses such as AAV, retroviruses, and Antiviruses having components that provide for virus integration such as the LTR sequences of retroviruses or lentivirus and the ITR sequences of AAV (Kootstra et al., Ann. Rev. Pharm. Toxicol., 43:413-439, 2003).

Viral Vectors

In one aspect, the invention provides expression vectors for the expression of the blocking and/or stimulating agent(s) that are viral vectors. Many viral vectors useful for gene therapy are known (see, for example, Lundstrom, Trends Biotechnol., 21:117, 122, 2003.

Preferred viral vectors include those selected from the group consisting of Antiviruses (LV), retroviruses (RV), adenoviruses (AV), adeno-associated viruses (AAV), and alpha viruses, though other viral vectors may also be used. For in vivo uses, viral vectors that do not integrate into the host genome are preferred, such as alpha viruses and adenoviruses, with alpha viruses being especially preferred. Preferred types of alpha viruses include Sindbis virus, Venezuelan equine encephalitis (VEE) virus, and Semliki Forest virus (SFV), with SFV being especially preferred. See, for example, Lundstrom, Expert Opin. Biol. Then 3:771-777, 2003; Afanasieva et al. Gene Then, 10:1850-59, 2003. For in vitro uses, viral vectors that integrate into the host genome are preferred, such as retroviruses, AAV, and Antiviruses.

In a preferred embodiment, the viral vector provides for transient high level expression in a transduced human cell.

In one embodiment, the viral vector does not provide for integration of the blocking and/or stimulating agent encoding nucleic acid into the genome of a transduced human cell.

In another embodiment, the viral vector provides for integration of a blocking and/or stimulating agent encoding nucleic acid into the genome of a transduced human cell.

In one embodiment, the invention provides methods of transducing a human cell in vivo, comprising contacting a solid tumor in vivo with an viral vector of the invention.

In another embodiment, the invention provides methods of transducing a human cell ex vivo, comprising contacting a human cell ex vivo with the blocking and/or stimulating agent viral vector of the invention. In one embodiment, the human cell is a tumor cell. In one embodiment, the human cell is allogeneic. In one embodiment, the tumor cell is derived from the patient. In one embodiment, the human cell is a non-tumor cell, such as, e.g., an antigen presenting cell (APC), or a T cell.

Virus particle coats may be modified to alter specificity and improve cell/tissue targeting, as is well known in the art. Viral vectors may also be delivered in other vehicles, for example, liposomes. Liposomes may also have targeting moieties attached to their surface to improve cell/tissue targeting.

The present application is directed to human cells expressing the blocking and/or stimulating agent. In a preferred embodiment, the human cell expresses a stimulating agent to ICOS (e.g., ICOSL, which may be secreted or expressed as a cell surface protein) that specifically binds to the extracellular domain of ICOS and activates ICOS mediated negative signaling. In certain embodiments, the human cell expresses the ICOS ligand proximal to a tumor cell for example in a cancer patient. Thus, the human cell is capable of localized expression of the ligand at a tumor cell or tumor cell mass. The ICOS ligand can activate ICOS signaling in cells proximal to said tumor cell, and/or break immune tolerance against a tumor-associated self antigen and stimulate an autoreactive T cell response to said tumor cell. In a preferred embodiment, localized expression of the ICOS ligand reduces or inhibits undesired adverse immune responses.

It is not necessary for the practice of the invention that the mechanism of action be understood. The cells and methods described herein provide human cells proximal to tumor cells or tumor cell masses. Expression of stimulating agents to ICOS and optionally blocking agents to T cell inhibitory proteins or additional cytokines in proximity to the tumor cells enhances anti-tumor immune responses.

Methods of Treatment

Described herein is a method of treating a patient afflicted with a cancer comprising administering to the patient a pharmaceutical composition comprising a pharmacologically effective amount of a blocking agent to a T cell inhibitory receptor and stimulating agent to ICOS. The method described herein is directed toward the treatment of cancer, e.g., leukemias and solid tumors (e.g., melanomas, carcinomas, sarcomas, lymphomas, etc.). More common solid cancers include bladder cancer, bone cancer (osteosarcoma), colorectal cancer, brain cancer, breast cancer, cervical cancer, oesophageal cancer, Hodgkin's lymphoma, kidney cancer, liver cancer, lung cancer, mesothelioma, multiple myeloma, non-Hodgkin's lymphoma, ovarian cancer, pancreatic cancer, penile cancer, prostate cancer, skin cancer (melanoma and non-melanoma) soft tissue carcinoma, gastric cancer, testicular cancer, thyroid cancer and endometrial cancer.

The administered pharmaceutical compositions will often further comprise one or more buffers (e.g., neutral buffered saline or phosphate buffered saline), carbohydrates (e.g., glucose, mannose, sucrose or dextrans), mannitol, proteins, polypeptides or amino acids such as glycine, antioxidants (e.g., ascorbic acid, sodium metabisulfite, butylated hydroxytoluene, butylated hydroxyanisole, etc.), bacteriostats, chelating agents such as EDTA or glutathione, solutes that render the formulation isotonic, hypotonic or weakly hypertonic with the blood of a recipient, suspending agents, thickening agents, preservatives, flavoring agents, sweetening agents, and coloring compounds as appropriate.

While any suitable carrier known to those of ordinary skill in the art may be employed in the compositions, the type of carrier will typically vary depending on the mode of administration. The therapeutic compositions may be formulated for any appropriate manner of administration, including for example, oral, nasal, mucosal, rectal, vaginal, topical, intravenous, intraperitoneal, intradermal, subcutaneous, and intramuscular administration.

For parenteral administration, the compositions can be administered as injectable dosages of a solution or suspension of the blocking agents of one or more T cell inhibitory receptors, the stimulating agents of ICOS, an expression vector expressing one or more blocking agents to a T cell inhibitory receptor and/or stimulating agent of ICOS, cells transformed with expression vectors expressing one or more blocking agents to a T cell inhibitory receptor and/or stimulating agent of ICOS, or a combination thereof, in a physiologically acceptable diluent with a pharmaceutical carrier that can be a sterile liquid such as sterile pyrogen free water, oils, saline, glycerol, polyethylene glycol or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, non-aqueous solutions of peanut oil, soybean oil, corn oil, cottonseed oil, ethyl oleate, and isopropyl myristate.

The blocking and/or stimulating agents described herein (including expression vectors and/or transformed cells expressing such blocking and/or stimulating agents) may be presented in unit-dose or multi-dose containers, such as sealed infusion bags, ampoules or vials. Such containers are typically sealed in such a way to preserve the sterility and stability of the formulation until use. In general, formulations may be preserved as suspensions, solutions or emulsions in oily or aqueous vehicles, as indicated above. Alternatively, a pharmaceutical composition may be preserved in a freeze-dried condition requiring only the addition of a sterile liquid carrier immediately prior to use.

The amount administered to the host will vary depending upon what is being administered, the purpose of the administration, such as prophylaxis or therapy, the state of the host, the manner of administration, the number of administrations, interval between administrations, and the like. These can be determined empirically by those skilled in the art and may be adjusted for the extent of the therapeutic response. Factors to consider in determining an appropriate dose include, but is not limited to, size and weight of the patient, the age and sex of the patient, the severity of the symptom, the stage of the disease, method of delivery of the agent, half-life of the agents, and efficacy of the agents. Stage of the disease to consider includes whether the disease is acute or chronic, relapsing or remitting phase, and the progressiveness of the disease.

Determining the dosages and times of administration for a therapeutically effective amount are well within the skill of the ordinary person in the art. For example, an initial effective dose can be estimated from cell culture or other in vitro assays. A dose can then be formulated in animal models to generate a circulating concentration or tissue concentration, including that of the IC50 as determined by the cell culture assays.

In addition, toxicity and therapeutic efficacy are generally determined by cell culture assays and/or using experimental animals, typically by determining a LD50 (lethal dose to 50% of the test population) and $ED_{50}$ (therapeutically effectiveness in 50% of the test population). Guidance is found in standard reference works, for example, Goodman & Gilman's The Pharmacological Basis of Therapeutics, 10th Ed. (Hardman, J. G. et al., eds.) McGraw-Hill, New York, N.Y. (2001).

For the purposes of this invention, the methods of administration are chosen depending on the condition being treated and the pharmaceutical composition. Administration of the blocking and or stimulating agent(s) can be done in a variety of ways, including, but not limited to, subcutaneously, intravenously, intraperitoneally, intramuscularly, and possibly direct injection to specified organs or tumors, although systemic administration is preferred. Administration of the pharmaceutical compositions may be through a single route or concurrently by several routes.

The compositions may be administered once per day, a few or several times per day, or even multiple times per day, depending upon, among other things, the indication being treated and the judgment of the prescribing physician.

The amount of blocking and/or stimulating agent needed for achieving a therapeutic effect may be determined empirically in accordance with conventional procedures for the particular purpose. Generally, for administering the cells for therapeutic purposes, the cells are given at a pharmacologically effective dose. "Pharmacologically effective amount" or "pharmacologically effective dose" refers to an amount sufficient to produce the desired physiological effect or amount capable of achieving the desired result, particularly for treating the disorder or disease condition, including reducing or eliminating one or more symptoms or manifestations of the disorder or disease. As an illustration, administration of cells to a patient suffering from cancer provides a therapeutic benefit not only when the underlying condition is eradicated or ameliorated, but also when the patient reports a decrease in the severity or duration of the symptoms associated with the disease, e.g., a decrease in tumor burden including disseminated tumor cells (DTC), a decrease in circulating tumor cells, an increase in progression free survival. Therapeutic benefit also includes halting or slowing the progression of the underlying disease or disorder, regardless of whether improvement is realized. Pharmacologically effective dose, as defined above, will also apply to therapeutic compounds used in combination with the cells, as further described below.

Preferably, the effect will result in a quantifiable change of at least about 10%, preferably at least 20%, 30%, 50%, 70%, or even 90% or more. Therapeutic benefit also includes halting or slowing the progression of the underlying disease or disorder, regardless of whether improvement is realized. When the combination of a blocking agent of a T cell inhibitory receptor and a stimulating agent of ICOS is used in with other treatment protocols, an effective amount is in ratio to a combination of components and the effect is not limited to individual components alone.

A pharmacologically effective amount that will treat cancer will modulate the symptoms typically by at least about 10%; usually by at least about 20%; preferably at least about 30%; or more preferably at least about 50%. Such will result in, e.g., statistically significant and quantifiable changes in the numbers of cells being affected. This may be a decrease in the numbers of micrometastases in distant organs, a decrease in recurrent metastatic disease, etc.

The blocking and stimulating agents described herein may be combined with other antitumor treatments, e.g., surgical resection, radiation therapy, chemotherapy, immunotherapy, and supportive therapy (e.g., painkillers, diuretics, antidiuretics, antivirals, antibiotics, nutritional supplements, anemia therapeutics, blood clotting therapeutics, bone therapeutics, and psychiatric and psychological therapeutics). Such other antitumor treatments, including treatment with one or more blocking agents to one or more T cell inhibitory receptors, may be provided sequentially (e.g., before or after) or simultaneously with the administration of the stimulating agent of ICOS.

EXAMPLES

Example 1

Stimulating Agents to ICOS Enhance the Anti-tumor Effects of Anti-CTLA-4 Antibody and Anti-PD-L1 Antibody

Example 1.1

Effect of a Stimulating Agent to ICOS Antibody on CD4$^+$ T Cell Proliferation

CD4+ T cells were prepared from C57BL/6 mice spleen by Dynal murine CD4+ T cell negative selection kit according to the manufacturer's instruction. Fifty thousand CD4+ T cells were stimulated in a 96 well plate pre-coated with or without anti-CD3 mAb (0.5 µg/ml) and 2 µg/ml of anti-CD28, 5 µg/ml of anti-ICOS mAb (clones C398.4A and 7E.17G9). Cells were incubated at 37° C., in a 5% of $CO_2$, for 72 hr and 1 µci of 3H-thymidine was added into each well 8 hr before the end of the culture. Plate was harvested and analyzed for 3H-thymidine incorporation.

As shown in FIG. 1, anti-ICOS antibodies enhanced proliferation of CD4$^+$ T cells in the presence of anti-CD3 antibody.

Example 1.2

Indirect Correlation Between Anti-CTLA-4 Induced ICOS Expression and Tumor Growth Mice were challenged with 2×10$^4$B16/F10 tumor cells. Mice were untreated or treated. Treated animals received 200 µg anti-CTLA-4 antibody on day 3 and 100 µg anti-CTLA-4 antibody on days 6, 9, 12, 15, 18, and 21 post tumor challenge. Tumor growth and levels of ICOS on CD4$^+$ FOXP3$^-$ effector T cells in the blood were monitored every three days.

Figure 2:
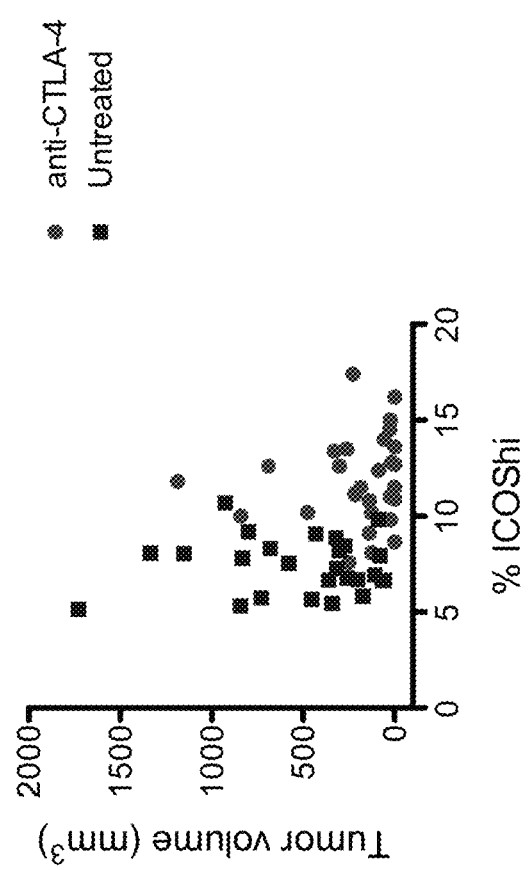
FIG. 2 shows the inverse correlation in untreated animals or animals treated with anti-CTLA-4 antibody after three weeks between tumor volume (mm$^3$; y-axis) and percent (%) ICOS expression by CD4$^+$Foxp3$^-$ cells (x-axis).
Figure 3:
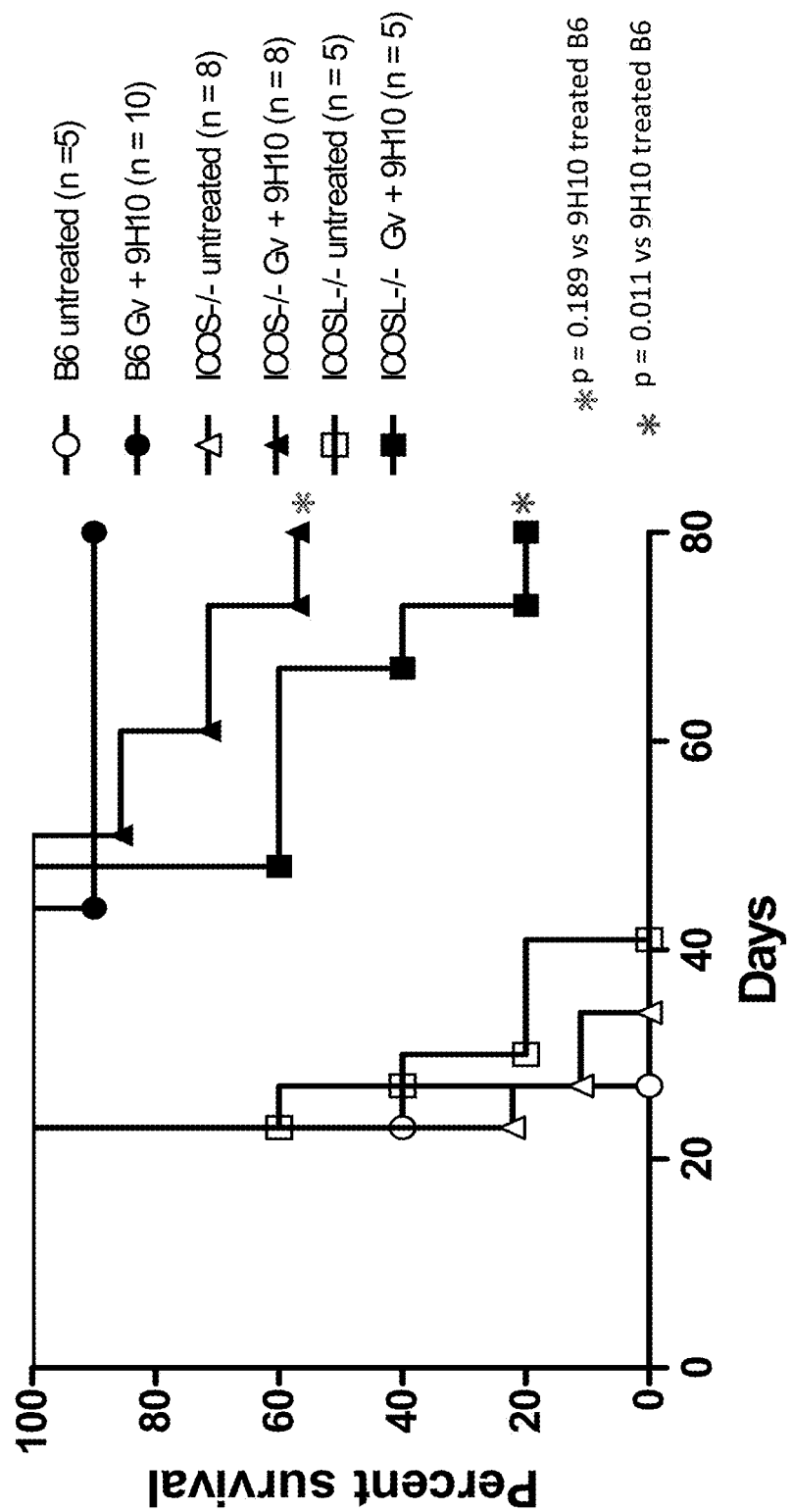
FIG. 3 demonstrates the percent survival of B16 tumor bearing ICOS$^+$/ICOSL$^+$ animals that were untreated, ICOS$^+$/ICOSL$^{+-}$ animals treated with GVAX and anti-CTLA-4 antibody (9H10), ICOS$^-$/ICOSL$^+$ animals that were untreated, ICOS$^-$/ICOSL$^+$ animals that were treated with GVAX and anti-CTLA-4 antibody (9H10), ICOS$^+$/ICOSL$^-$ animals that were untreated, and ICOS$^+$/ICOSL$^-$ animals treated with GVAX and anti-CTLA-4 antibody (9H10).

As shown in FIG. 2, CD4$^+$FOXP3$^-$ cells isolated from treated animals expressed increased levels of ICOS. Additionally, the increased expression of ICOS indirectly correlated with tumor burden (FIG. 2).

Example 1.3

ICOS$^-$ or ICOSL$^-$ Mice Demonstrated a Reduced Anti-tumor Response Mediated by Anti-CTLA-4 Antibody Wild type C57BL/6, ICOS deficient C57BL/6, and ICOS-ligand (ICOSL) deficient C57BL/6 mice bearing B16/BL6 tumors were either left untreated or treated s.c. (on day 3 post-tumor implantation) with 1×10$^6$ irradiated GM-CSF-producing B16 (GVAX) and anti-CTLA-4 i.p. (9H10), at a dosing of 0.2, 0.1 and 0.1 mg on days 3, 5 and 7, respectively. Tumor growth was monitored and percent survival calculated on day 80.

Wild type, ICOS deficient, or ICOSL deficient mice bearing tumors and left untreated died between 25 and 41 days after tumor implantation (open circle, open triangle and open square respectively). Conversely, 90% survival was observed when wild type mice were treated with GVAX and anti-CTLA-4 combination therapy (closed circles). Remarkably, ICOS deficient (closed triangles) and ICOSL deficient mice (closed squares) showed significantly lower protection after being treated with GVAX and anti-CTLA-4 antibody, demonstrating a key role for this ligand/receptor pair interaction during GVAX/anti-CTLA-4 combination therapy.

Example 1.4

Enhanced Anti-Tumor Effect Using GVAX, Anti-CTLA-4 Antibody, and Anti-ICOS Antibody Mice challenged with 5×10$^4$B16/BL6 tumor cells were (1) untreated, (2) treated with 1×10$^6$ irradiated GM-CSF-producing B16 only (GVAX; s.c. 3, 6, and 9 days post-implantation), (2) treated with 1×10$^6$ irradiated GVAX (s.c. 3, 6, and 9 days post-implantation), 200 µg anti-CTLA-4 antibody (day 3 post-tumor implantation), and 100 µg anti-CTLA-4 antibody (days 6, 9, 13, and 17 post-tumor implantation), or (3) treated with 1×10$^6$ irradiated GVAX (3, 6, and 9 days post-implantation), 200 µg anti-CTLA-4 antibody (day 3 post-tumor implantation), 100 µg anti-CTLA-4 antibody (days 6, 9, 13, and 17 post-tumor implantation) and 200 μg anti-ICOS antibody (days 3, 6, 9, 13, and 17 post-tumor implantation). Tumor growth was monitored and survival was calculated on day 80.

Figure 4:
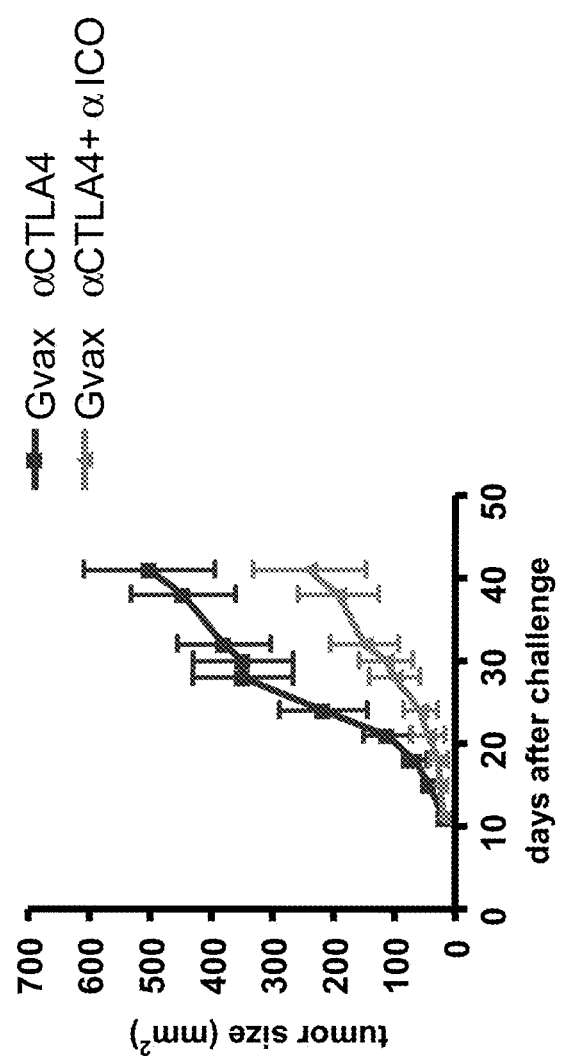
FIG. 4 shows tumor size (mm$^3$; y-axis) 0-50 days after tumor challenge (x-axis) in animals treated with GVAX and anti-CTLA-4 antibody (αCTLA4) or animals treated with GVAX, anti-CTLA-4 antibody (αCTLA4) and anti-ICOS antibody (αICO).
Figure 5:
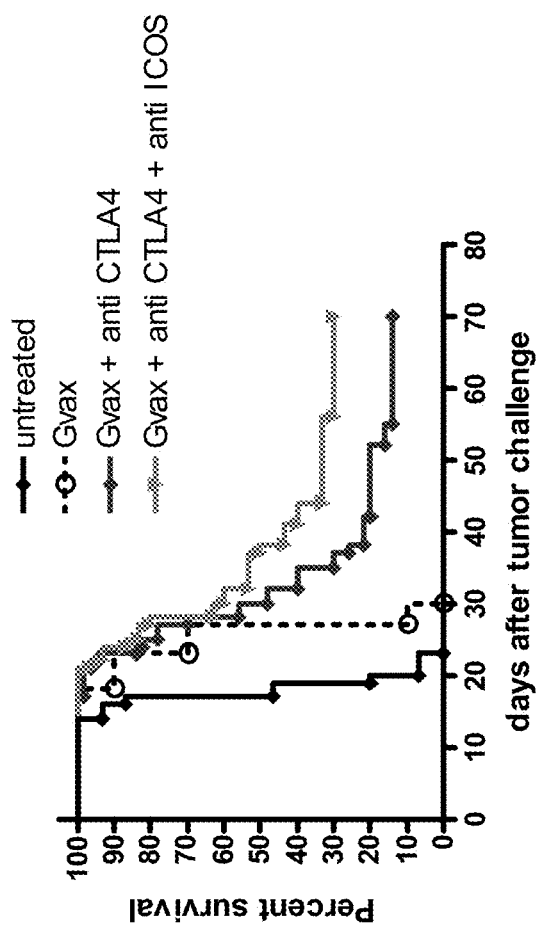
FIG. 5 shows percent survival of B16/BL6 tumor bearing animals that were untreated, treated with GVAX, treated with GVAX and anti-CTLA-4 antibody, or treated with GVAX, anti-CTLA-4 antibody and anti-ICOS antibody.

As shown in FIG. 4, treating animals with a combination of GVAX, anti-CTLA-4 antibody and anti-ICOS antibody resulted in delayed tumor growth compared to treating animals with GVAX and anti-CTLA-4 antibody only. This finding is consistent with the finding that mice treated with GVAX with anti-CTLA-4 and anti-ICOS antibodies exhibit higher survival rates compared to mice treated with GVAX and anti-CTLA4 antibody only (FIG. 5).

Example 1.5

Enhanced Anti-tumor Effect Using Anti-ICOS and Anti-PD-L1 Antibodies

Three-day B16/BL6-bearing mice were either untreated or treated s.c. (on day 3 post-tumor implantation) with $1 \times 10^6$ irradiated GM-CSF-producing B16 (GVAX) and i.p. anti-ICOS antibody (7E.17G9), anti-PD-L1 antibody (10F.9G2) or the combination at a dosing of 0.2, 0.1 and 0.1 mg on days 3, 5 and 7 respectively. Tumor growth was monitored and percent survival calculated on day 80.

Figure 6:
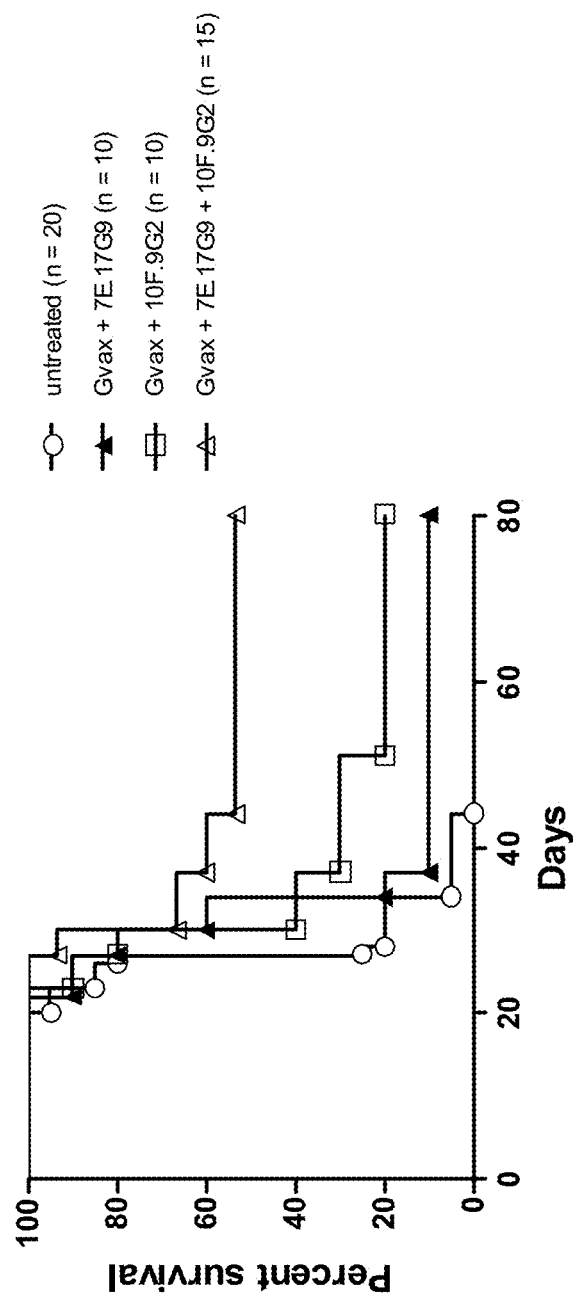
FIG. 6 shows percent survival of B16/BL6 tumor bearing animals that were untreated, treated with GVAX and anti-ICOS (7E.17G9) antibody, treated with GVAX and anti-PD- L1 antibody (10F.9G2), or treated with GVAX, anti-PD-L1 antibody and anti-ICOS antibody.

Mice treated with a combination of GVAX and anti-ICOS antibody, or GVAX and anti-PD-L1 antibody demonstrated poor survival rates (FIG. 6). In contrast, combination therapy using anti-PD-L1 antibody, anti-ICOS antibody and GVAX resulted in 50% survival, demonstrating a potent synergistic effect obtained with the combination of anti-ICOS antibody (7E.17G9) with anti-PD-L1 antibody (10F.9G2) and GVAX.

Example 2

Use of ICOS Ligand Expressing Tumor Cells as an Anti-tumor Vaccine

Example 2.1

Example 2.1.1

Antibodies

Anti-CTLA4 (clone 9H10) was purchased from Bio X Cell.

Example 2.1.2

Cell Lines

The highly tumorigenic and poorly immunogenic melanoma cell line B16/BL6 was used for tumor challenge. B16/BL6-expressing GM-CSF, here referred to as GVAX, was used for treatment of tumor-bearing mice. B16-Thy1.1 was generated through retroviral transduction of B16/BL6 cells with the vector MSCV-IRES-Thy1.1 which was a gift from Dr. Leo lefrancois at University of Connecticut. B16-mICOSL was generated through retroviral transduction of B16/BL6 cells with the vector MSCV-ICOSL expressing full length of mouse ICOSL (gift from Dr. William Sha, University of California, Berkeley). GVAX cells were also transduced with the MSCV-ICOSL vector to generate GVAX-mICOSL.

Example 2.1.3

Tumor Challenge and Treatment Experiments

Mice were injected in the right flank i.d. on day 0 with 50,000 B16/BL6 melanoma cells and treated on days 3, 6, 9, and 12 with $7.5 \times 10^5$ irradiated (150 Gy) GVAX mixed with $7.5 \times 10^5$ irradiated (150 Gy) B16/BL6-Thy1.1 (n=10) or B16-mICOSL (n=10) on the left flank, in combination with 100 μg anti-CTLA4 i.p. (200 μg on day 3). Tumor growth and rejection were monitored over time.

Mice were injected in the right flank i.d. on day 0 with 20,000 B16/BL6 melanoma cells and treated or not on days 3, 6, 9, and 12 with $1 \times 10^6$ irradiated (150 Gy) GVAX (n=10) or GVAX-mICOSL (n=10) on the left flank, in combination with 100 μg anti-CTLA4 i.p. (200 μg on day 3). Tumor growth and rejection were monitored over time.

Mice were injected in the right flank i.d. on day 0 with 20,000 B16/BL6 melanoma cells and treated or not on days 3, 6, 9, and 12 with $1 \times 10^6$ irradiated (150 Gy) B16/BL6-Thy1.1 (n=10) or B16-mICOSL (n=10) on the left flank, with or without 100 μg anti-CTLA4 i.p. (200 μg on day 3). Tumor growth and rejection were monitored over time.

Mice were injected in the right flank i.d. on day 0 with 20,000 B16/F10 melanoma cells and treated or not on days 3, 6, 9, and 12 with $1 \times 10^6$ irradiated (150 Gy) B16-mICOSL (n=5) on the left flank, with or without 100 μg anti-CTLA4 i.p. (200 μg on day 3). Tumor growth and rejection were monitored over time.

Example 2.2

Results

Figure 7:
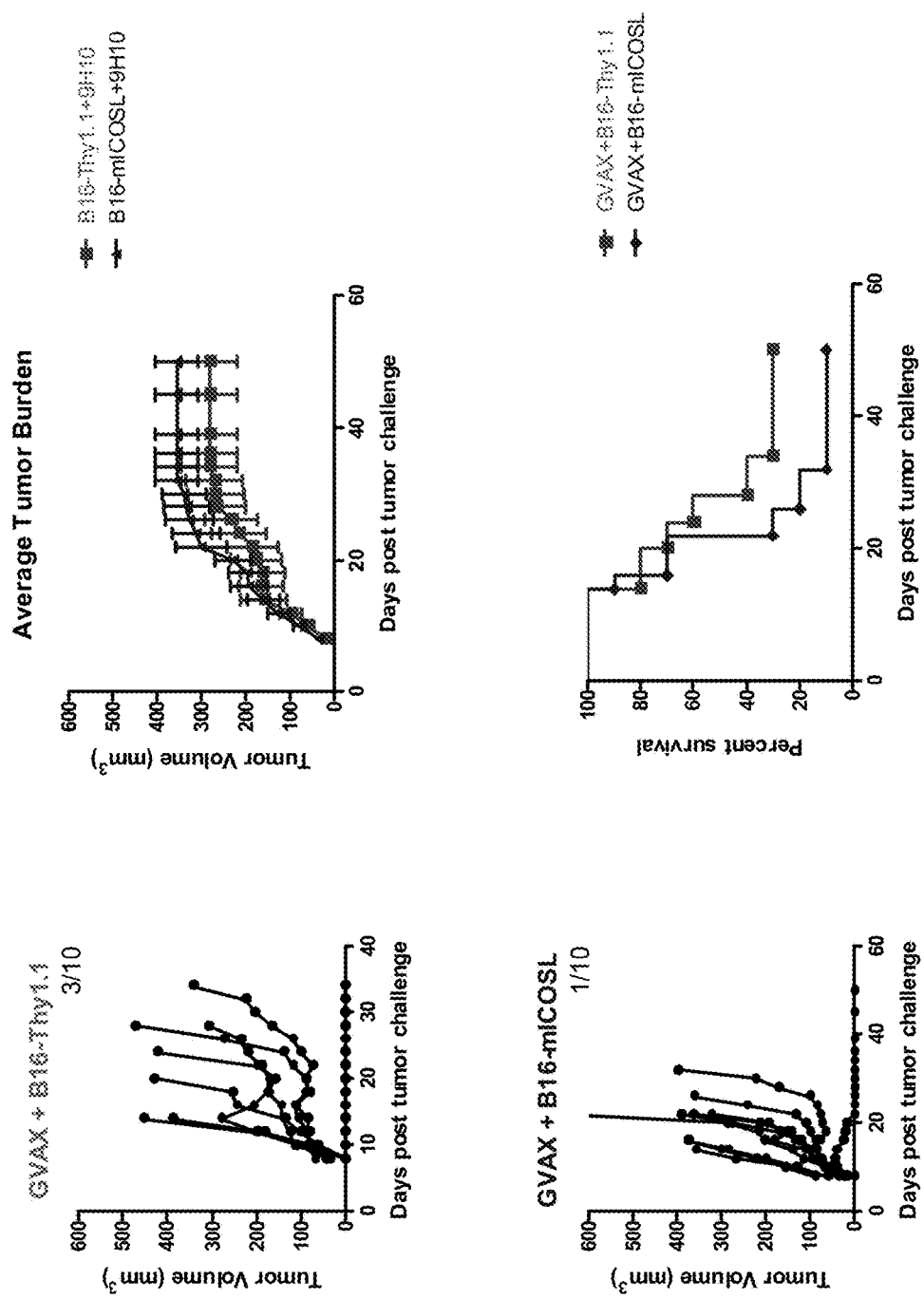
FIG. 7 shows the individual tumor growth curves of each animal (left column), average tumor volumes in each treatment group (upper right corner), and survival curves of each treatment group (bottom right corner) of animals treated with GVAX and B16/BL6 cells transduced to express Thy1.1 (B16-Thy1.1) or B16/BL6 cells transduced to express membrane-bound ICOSL (B16-mICOSL). The numbers in the individual tumor growth curves indicate the percentage of tumor-free mice at the end of the experiment. For the survival curves, a mouse was considered dead when the tumor volume reached 300 mm$^3$.
Figure 8:
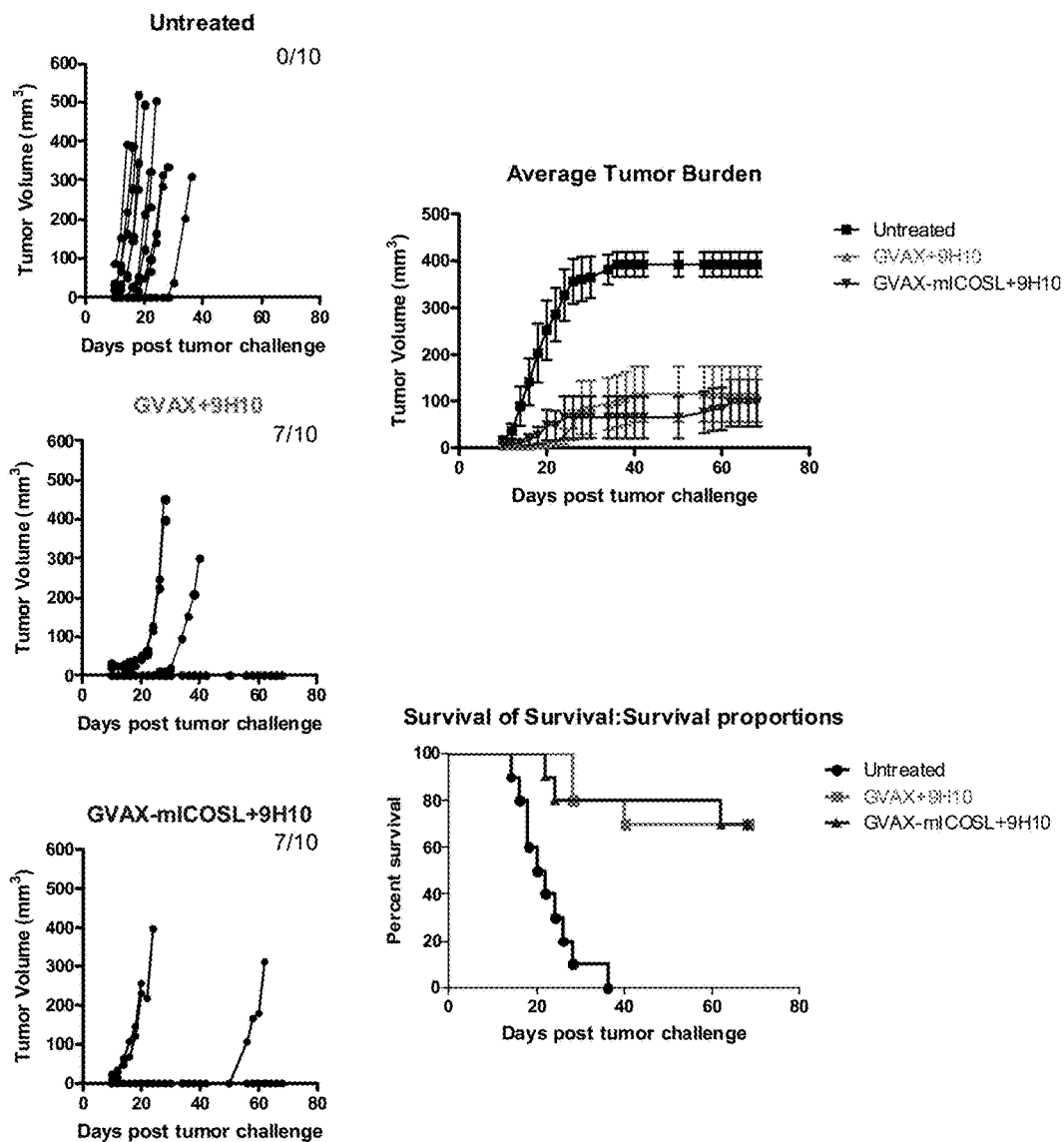
FIG. 8 shows the individual tumor growth curves of each animal (left column), average tumor volumes in each treatment group (upper right corner) and survival curves of each treatment group (bottom right corner) of animals treated with GVAX and anti-CTLA-4 antibody (9H10) alone or in combination with B16/BL6 cells transduced to express membrane-bound ICOSL (mICOSL). The numbers in the individual tumor growth curves indicate the percentage of tumor-free mice at the end of the experiment. For the survival curves, a mouse was considered dead when the tumor volume reached 300 mm$^3$.
Figure 9:
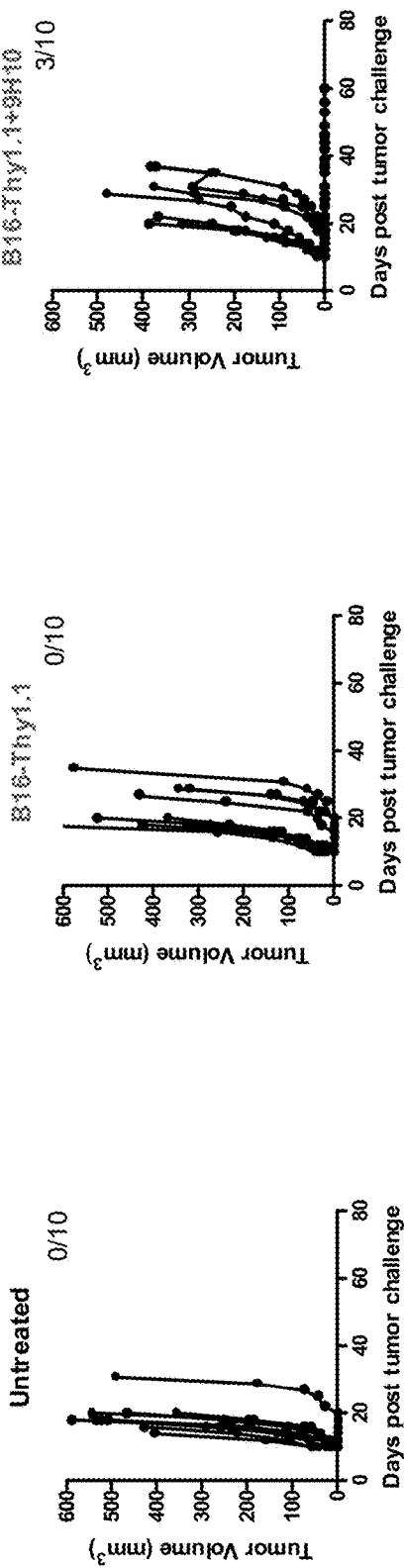
FIG. 9 shows individual tumor growth curves from a first experiment of B16/BL6 in mice that were untreated or treated with B16/BL6 cells transduced to express Thy1.1 (B16-Thy1.1) in the absence or presence of anti-CTLA-4 antibody (9H10) or B16/BL6 cells transduced to express membrane-bound ICOSL (B16-mICOSL) in the absence or presence of anti-CTLA-4 antibody (9H10). The numbers indicate the percentage of tumor-free mice at the end of the experiment.
Figure 9:
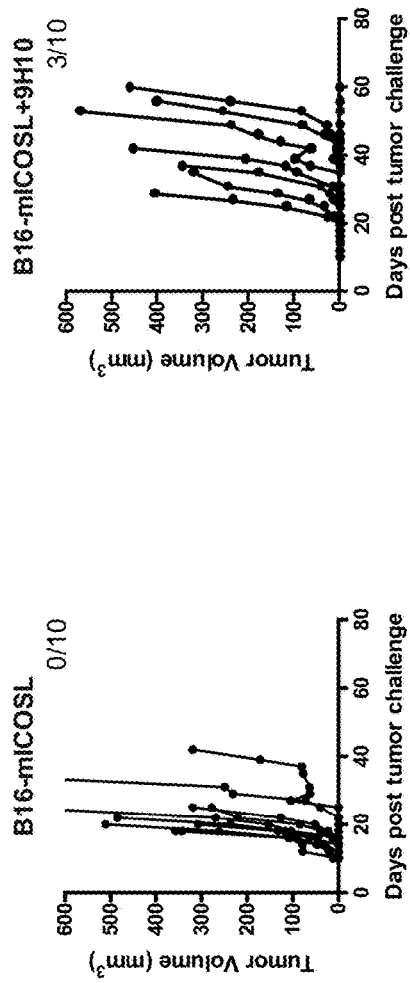
Figure 10:
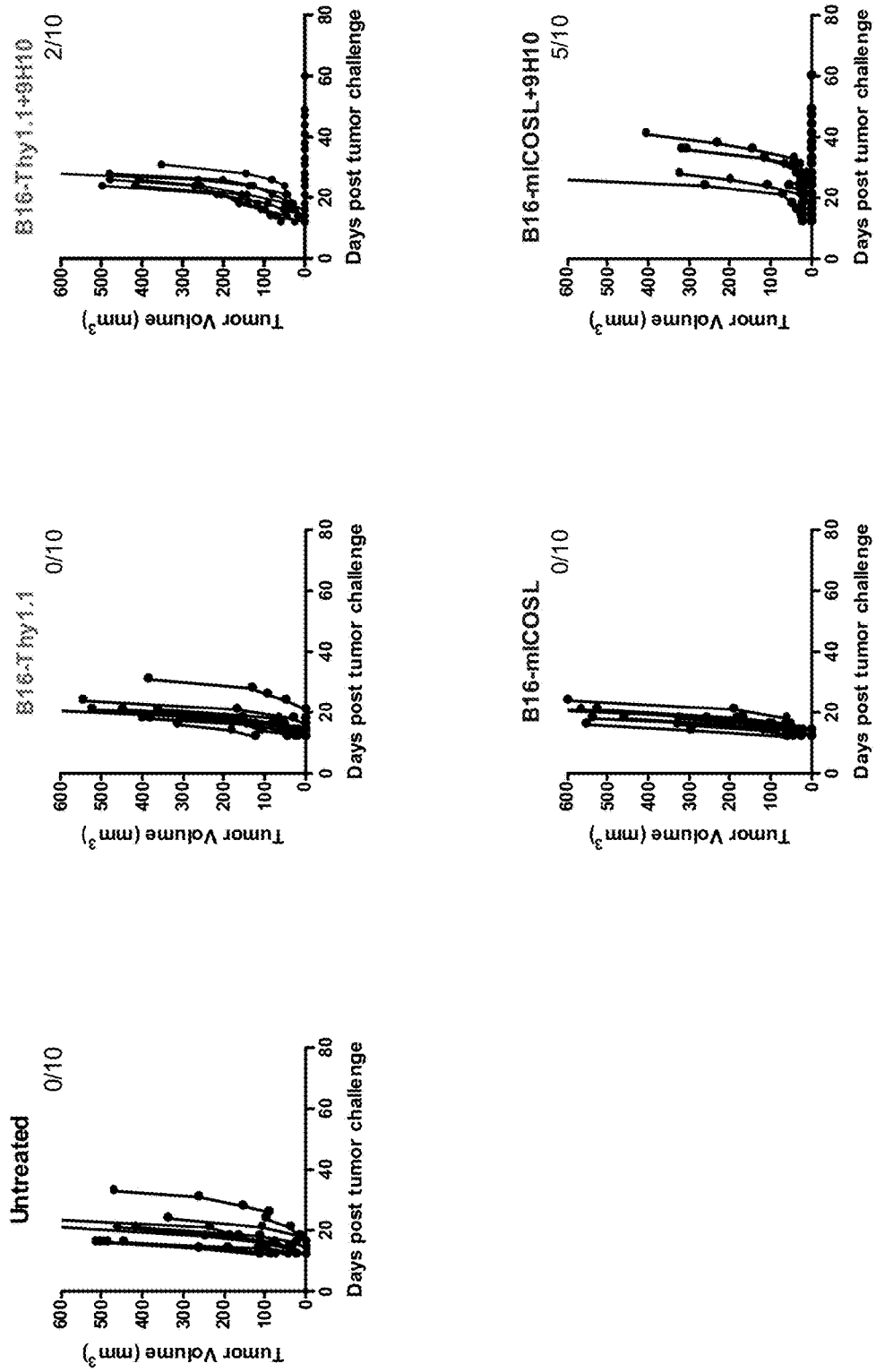
FIG. 10 shows individual tumor growth curves from a second experiment of B16/BL6 in mice that were untreated or treated with B16/BL6 cells transduced to express Thy1.1 (B16-Thy1.1) in the absence or presence of anti-CTLA-4 antibody (9H10) or B16/BL6 cells transduced to express membrane-bound ICOSL (B16-mICOSL) in the absence or presence of anti-CTLA-4 antibody (9H10). The numbers indicate the percentage of tumor-free mice at the end of the experiment.
Figure 11:
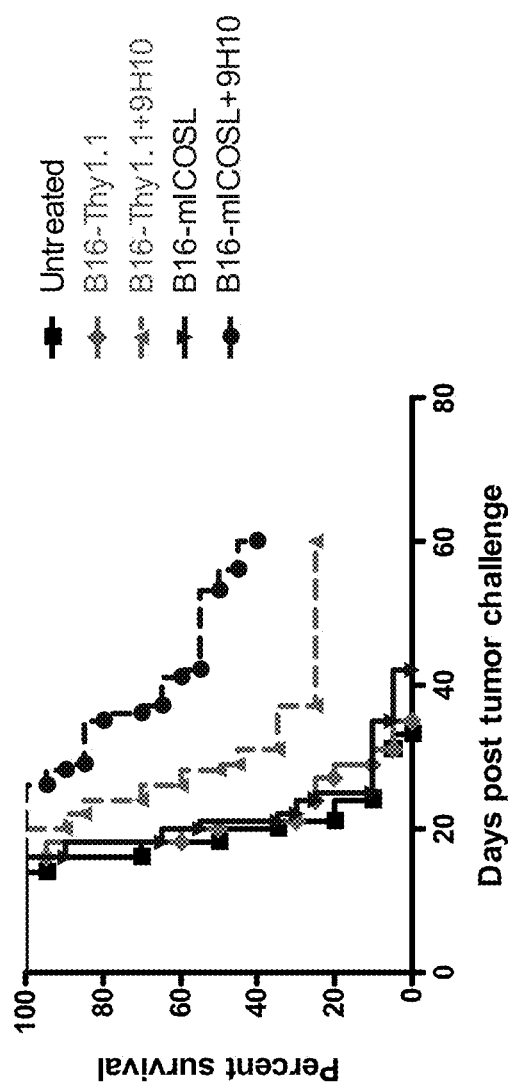
FIG. 11 shows the survival curves of each treatment group of B16/BL6 in mice that were untreated or treated with B16/BL6 cells transduced to express Thy1.1 (B16-Thy1.1) in the absence or presence of anti-CTLA-4 antibody (9H10) or B16/BL6 cells transduced to express membrane-bound ICOSL (B16-mICOSL) in the absence or presence of anti-CTLA-4 antibody (9H10).
Figure 12A:
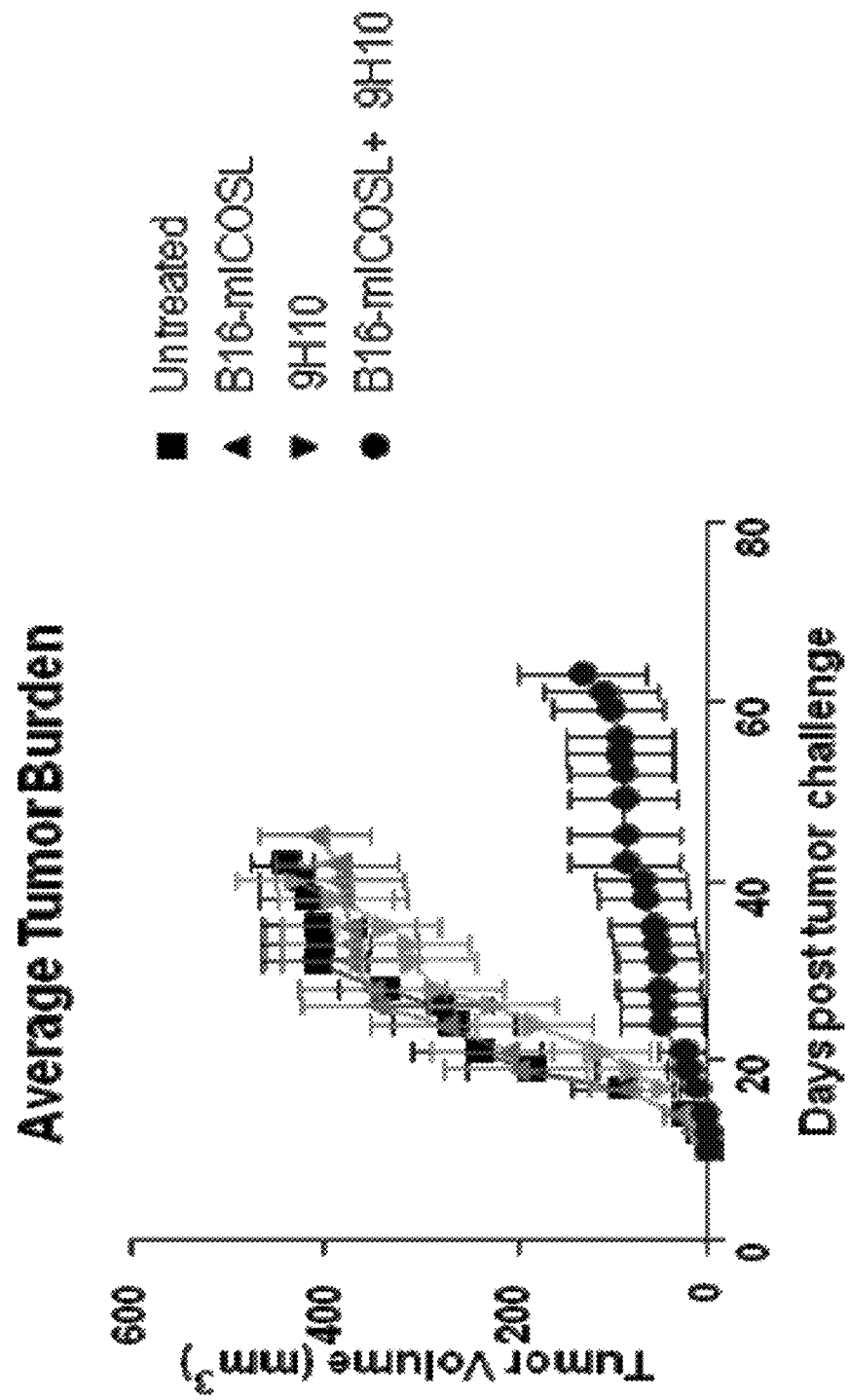
FIG. 12A shows average tumor growth curves of B16/BL6 in mice that were untreated or treated with B16/BL6 cells transduced to express membrane-bound ICOSL (B16-mICOSL) and/or anti-CTLA-4 antibody (9H10).
Figure 12B:
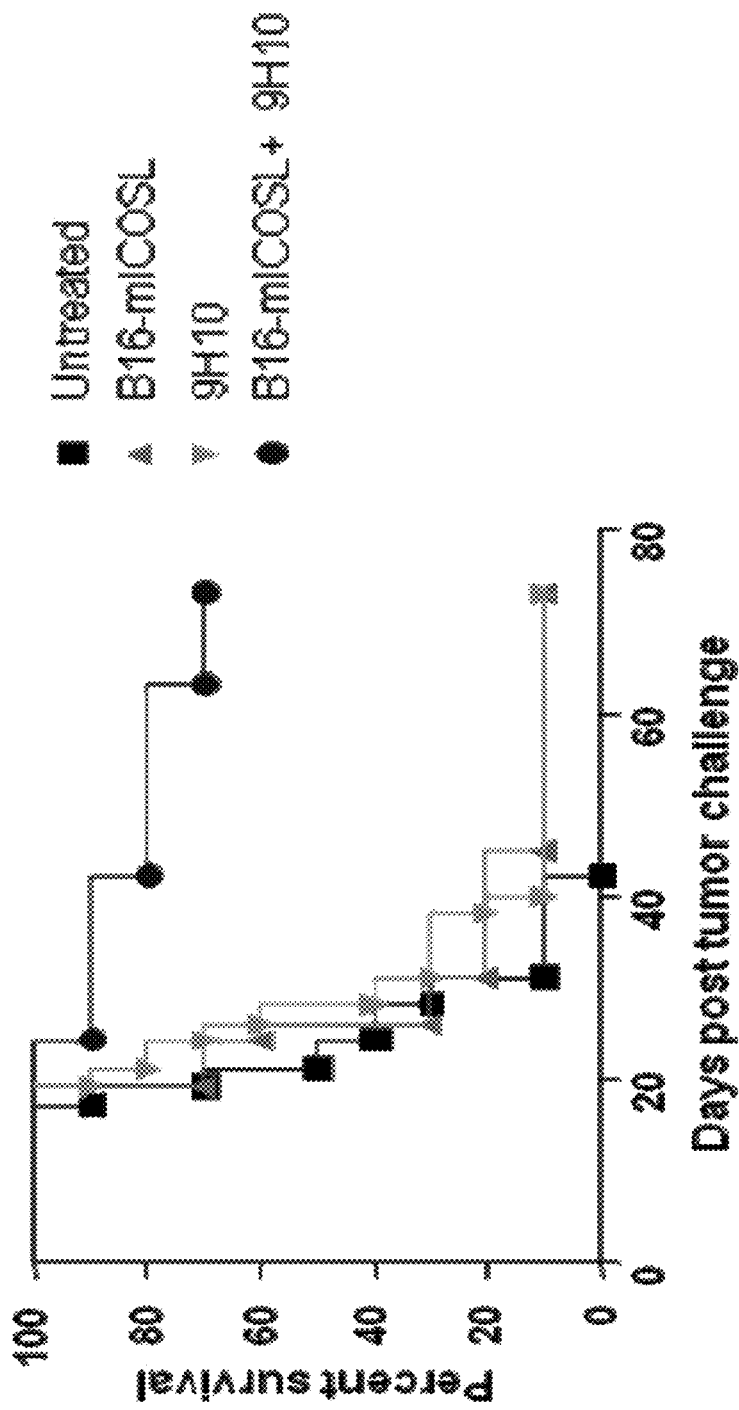
FIG. 12B shows the survival curves of each treatment group of B16/BL6 in mice that hat were untreated or treated with B16/BL6 cells transduced to express membrane-bound ICOSL (B16-mICOSL) and/or anti-CTLA-4 antibody (9H10). For the survival curves, a mouse was considered dead when the tumor volume reached 300 mm$^3$.

The B16 cellular vaccine expressing ICOSL, in the absence or presence of GVAX, did not add to the tumor protection rate beyond the previous combination therapy of GVAX and CTLA-4 blockade (FIGS. 7 and 8).

In the setting without GM-CSF, the B16 cellular vaccine expressing ICOSL has a synergistic effect together with CTLA-4 blockade to provide delay in tumor growth and/or overall advantage in tumor rejection (FIGS. 9-12).

All patents and patent publications referred to herein are hereby incorporated by reference.

Certain modifications and improvements will occur to those skilled in the art upon a reading of the foregoing description. It should be understood that all such modifications and improvements have been deleted herein for the sake of conciseness and readability but are properly within the scope of the following claims.

What is claimed is:

1. A method of treating cancer in a patient comprising administering to the patient a blocking anti-PD-1 antibody and an agonist anti-ICOS antibody.

2. The method of claim 1, wherein the blocking anti-PD-1 antibody and the agonist anti-ICOS antibody are administered simultaneously or sequentially.

3. The method of claim 1, wherein the agonist anti-ICOS antibody is a monoclonal antibody.

4. The method of claim 3, wherein the blocking anti-PD-1 antibody is a monoclonal antibody.

5. The method of claim 4, wherein the agonist anti-ICOS antibody is a humanized antibody.

6. The method of claim 3, wherein the blocking anti-PD-1 antibody is a humanized antibody.

7. The method of claim 1, wherein the agonist anti-ICOS antibody is a humanized antibody.

8. The method of claim 7, wherein the blocking anti-PD-1 antibody is a humanized antibody.

9. The method of claim 1 consisting of administering to the patient one or more doses of the blocking anti-PD-1 antibody and one or more doses of the agonist anti-ICOS antibody.

10. The method of claim 9, wherein at least one dose of the blocking anti-PD-1 antibody and at least one dose of the agonist anti-ICOS antibody are administered simultaneously or sequentially.

11. The method of claim 9, wherein the agonist anti-ICOS antibody is a monoclonal antibody.

12. The method of claim 11, wherein the blocking anti-PD-1 antibody is a monoclonal antibody.

13. The method of claim 12, wherein the agonist anti-ICOS antibody is a humanized antibody.

14. The method of claim 11, wherein the blocking anti-PD-1 antibody is a humanized antibody.

15. The method of claim 9, wherein the agonist anti-ICOS antibody is a humanized antibody.

16. The method of claim 15, wherein the blocking anti-PD-1 antibody is a humanized antibody.

17. The method of claim 4, wherein the method does not comprise administering another antitumor treatment.

18. The method of claim 4, wherein the method does not comprise administering another antitumor treatment other than surgical resection or radiation therapy.

19. The method of claim 4, wherein the method does not comprise administering another immunotherapy.

* * * * *